(12) United States Patent
Vidlund et al.

(10) Patent No.: US 9,986,993 B2
(45) Date of Patent: Jun. 5, 2018

(54) ADJUSTABLE TETHER AND EPICARDIAL PAD SYSTEM FOR PROSTHETIC HEART VALVE

(71) Applicant: Tendyne Holdings, Inc., Roseville, MN (US)

(72) Inventors: Robert M. Vidlund, Forest Lake, MN (US); Craig A. Ekvall, East Bethel, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 635 days.

(21) Appl. No.: 14/619,328

(22) Filed: Feb. 11, 2015

(65) Prior Publication Data

US 2015/0223934 A1   Aug. 13, 2015

Related U.S. Application Data

(60) Provisional application No. 61/938,275, filed on Feb. 11, 2014.

(51) Int. Cl.
*A61F 2/24*    (2006.01)
*A61B 17/04*   (2006.01)
*A61B 17/00*   (2006.01)

(52) U.S. Cl.
CPC ........ *A61B 17/0401* (2013.01); *A61F 2/2412* (2013.01); *A61F 2/2457* (2013.01);
(Continued)

(58) Field of Classification Search
CPC ........ A61F 2/24; A61F 2/2409; A61F 2/2418; A61F 2/2427
(Continued)

(56) References Cited

U.S. PATENT DOCUMENTS 2,697,008 A   12/1954   Rowley
3,409,013 A   11/1968   Berry
(Continued)

FOREIGN PATENT DOCUMENTS

CN    1486161        3/2004
CN    1961845 A      5/2007
(Continued)

OTHER PUBLICATIONS

US 9,155,620, 10/2015, Gross et al. (withdrawn)
(Continued)

*Primary Examiner* — Eric Rosen
*Assistant Examiner* — Mikail Mannan
(74) *Attorney, Agent, or Firm* — Cooley LLP

(57) ABSTRACT

Apparatus and methods are described herein for repositioning a tether attached to a prosthetic heart valve. In some embodiments, a method includes inserting a distal end portion of a snare device through an incision at a first location in a ventricular wall of a heart and within the left ventricle of the heart. A tether extending from a prosthetic mitral valve, through the left ventricle and out an incision at a second location on the ventricular wall of the heart is snared with the snare device. The tether is pulled with the snare device such that a proximal end of the tether is moved back through the incision at the second location on the ventricular wall and into the left ventricle. The snare device is pulled proximally such that the tether is pulled proximally through the incision at the first location in the ventricular wall of the heart.

14 Claims, 18 Drawing Sheets

(52) U.S. Cl.
CPC .............. *A61B 2017/00243* (2013.01); *A61B 2017/00349* (2013.01); *A61B 2017/00358* (2013.01); *A61B 2017/0417* (2013.01); *A61B 2017/0464* (2013.01); *A61B 2017/0496* (2013.01)

(58) Field of Classification Search
USPC ...................................................... 623/2.11
See application file for complete search history.

(56) References Cited

U.S. PATENT DOCUMENTS

| | | | |
|---|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 9/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |

(56) References Cited

U.S. PATENT DOCUMENTS

| | | |
|---|---|---|
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |

(56) References Cited

U.S. PATENT DOCUMENTS

| | | |
|---|---|---|
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |

(56) References Cited

U.S. PATENT DOCUMENTS

| | | |
|---|---|---|
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1* | 1/2011 | Lutter .................. A61F 2/2457 623/1.26 |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1* | 3/2011 | Thornton ......... A61B 17/00234 623/2.11 |
| 2011/0112632 A1* | 5/2011 | Chau .................... A61F 2/2418 623/2.11 |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |

(56) References Cited

U.S. PATENT DOCUMENTS

| | | |
|---|---|---|
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264206 A1 | 10/2011 | Tabor |
| 2011/0288637 A1 | 11/2011 | De Marchena |
| 2011/0319988 A1* | 12/2011 | Schankereli ......... A61F 2/2418 623/2.11 |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0283824 A1 | 11/2012 | Lutter et al. |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0358224 A1 | 12/2014 | Tegels et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127096 A1 | 5/2015 | Rowe et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |

(56) References Cited

FOREIGN PATENT DOCUMENTS

| | | |
|---|---|---|
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2009-514628 | 4/2009 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/070372 | 7/2006 |
| WO | WO 2006/113906 | 10/2006 |
| WO | WO 2006/127756 | 11/2006 |
| WO | WO 2007/081412 | 7/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |

OTHER PUBLICATIONS

Al Zaibag, M. et al., "Percutaneous Balloon Valvotomy in Tricuspid Stenosis," British Heart Journal, Jan. 1987, 57(1):51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R. et al., "Transluminal implantation of artificial heart valves. Description of a new expandable aortic valve and initial results with implantation by catheter technique in closed chest pigs," European Heart Journal, 1992, 13(5):704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Bernacca, G. M. et al., "Polyurethane heart valves: Fatigue failure, calcification, and polyurethane structure," Journal of Biomedical Materials Research, Mar. 5, 1997, 34(3):371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive CardioVascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142.html>, Dec. 10, 2012, 5 pages.

Gray, H., The Heart, Anatomy of the Human Body, 1918, Retrieved from the Internet <http://education.yahoo.com/reference/gray/subjects/subject/138>, Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

(56) References Cited

OTHER PUBLICATIONS

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardio-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2):194-198.

Moazami, N. et al., "Transluminal aortic valve placement: A feasibility study with a newly designed collapsible aortic valve," ASAIO Journal, Sep./ Oct. 1996, 42(5):M381-M385.

Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196(11):173-174.

Rashkind, W. J., "Historical Aspects of Interventional Cardiology: Past, Present, Future," Texas Heart Institute Journal, Dec. 1986, 13(4):363-367.

Reul, H. et al., "The Geometry of the Aortic Root in Health, at Valve Disease and After Valve Replacement," J. Biomechanics, 1990, 23(2):181-191.

Rosch, J. et al., "The Birth, Early Years and Future of Interventional Radiology," J Vasc Intery Radiol., Jul. 2003, 4:841-853.

Ross, D. N., "Aortic Valve Surgery," Guy's Hospital, London, 1968, pp. 192-197.

Rousseau, E. P. M. et al., "A mechanical analysis of the closed Hancock heart valve prosthesis," Journal of Biomechanics, 1988, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, J. B., "Experience with New Retrieval Forceps for Foreign Body Removal in the Vascular, Urinary, and Biliary Systems," Radiology, 1990, 176:535-538.

Serruys, P. W. et al., "Stenting of Coronary Arteries. Are we the Sorcerer's Apprentice?," European Heart Journal , Sep. 1989, 10(9):774-782.

"Shape Memory Alloys," Retrieved from the Internet: <http://webdocs.cs.ualberta.ca/~database/MEMS/sma.html>, Feb. 5, 2016, 3 pages.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, B. T. et al., "Modifications of Gianturco Expandable Wire Stents," Am. J. Roentgenol., May 1988, 150(5):1185-1187.

Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.

Webb, J. G. et al., "Percutaneous Aortic Valve Implantation Retrograde from the Femoral Artery," Circulation, 2006, 113:842-850.

Wheatley, D. J., "Valve Prostheses," Rob & Smith's Operative Surgery, Fourth Edition, 1986, pp. 415-424, Butterworths.

Yoganathan, A. P. et al., "The Current Status of Prosthetic Heart Valves," In Polymetric Materials and Artificial Organs, American Chemical Society, 1984, pp. 111-150.

\* cited by examiner

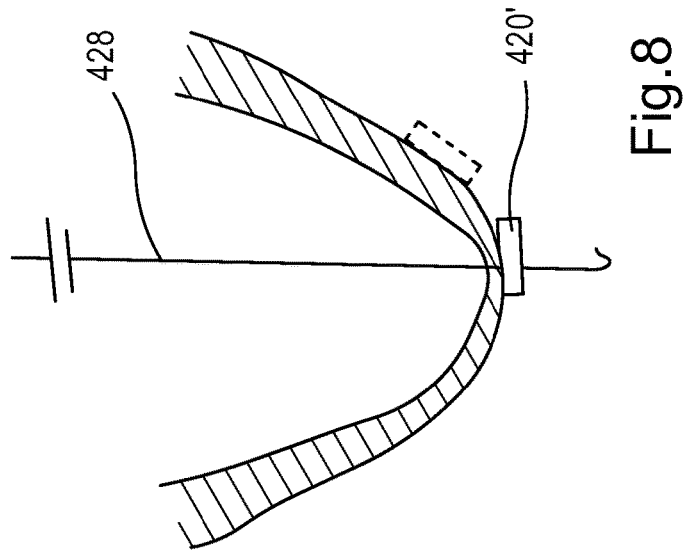
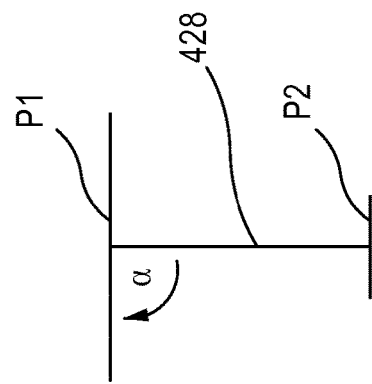
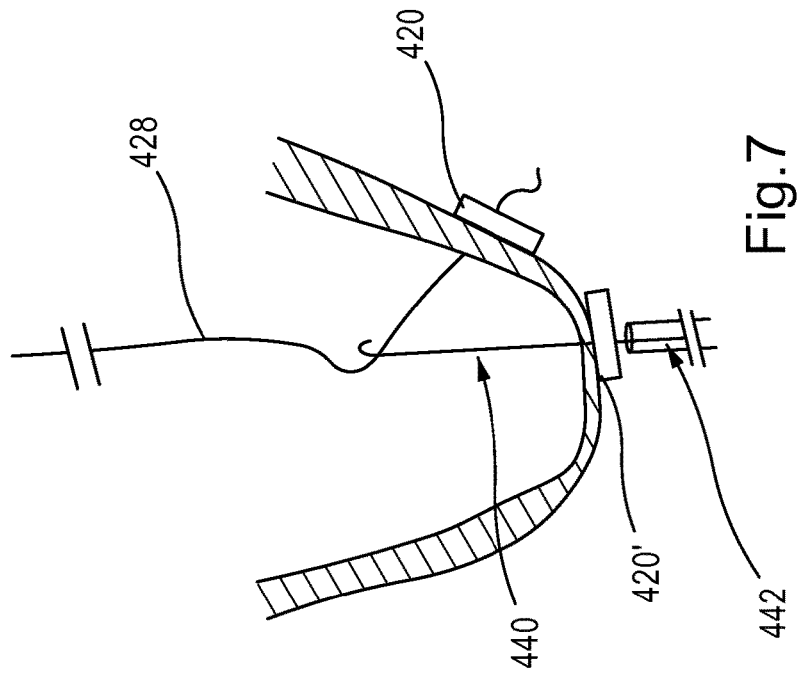

ADJUSTABLE TETHER AND EPICARDIAL PAD SYSTEM FOR PROSTHETIC HEART VALVE

CROSS-REFERENCE TO RELATED APPLICATIONS

This application claims priority to and the benefit of U.S. Provisional Patent Application No. 61/938,275, filed Feb. 11, 2014, entitled "Adjustable Tether and Epicardial Pad System for Prosthetic Mitral Valve," the disclosures of which is incorporated herein by reference in its entirety.

This application is also related to PCT international Application No. PCT/US2014/049218, filed Jul. 31, 2014, entitled "Epicardial Anchor Devices and Methods," (referred to herein as "the '218 PCT application"), the disclosure of which is incorporated herein by reference in its entirety.

BACKGROUND

Embodiments are described herein that relate to devices and methods for anchoring a prosthetic heart valve replacement.

A known design for a prosthetic mitral valve employs a tether coupled between the valve and the wall of the ventricle to help secure the prosthetic valve in the native valve apparatus. Problems can arise with a prosthetic valve employing such a tether if the tether is not properly tensioned or if the tether has been deployed in a less than optimal angular configuration or has migrated such that the valve axis is no long orthogonal to the annular plane.

Thus, a need exists for improved devices and methods for deploying and anchoring prosthetic heart valves, and that can provide the ability to adjust the tension on an anchoring tether and/or to reposition an anchor location for a prosthetic heart valve.

SUMMARY

Apparatus and methods are described herein for repositioning a tether attached to a prosthetic heart valve. In some embodiments, a method includes inserting a distal end portion of a snare device through an incision at a first location in a ventricular wall of a heart and within the left ventricle of the heart. A tether extending from a prosthetic mitral valve, through the left ventricle and out an incision at a second location on the ventricular wall of the heart is snared with the snare device. The tether is pulled with the snare device such that a proximal end of the tether is moved back through the incision at the second location on the ventricular wall and into the left ventricle. The snare device is pulled proximally such that the tether is pulled proximally through the incision at the first location in the ventricular wall of the heart.

BRIEF DESCRIPTION OF THE DRAWINGS

FIGS. 7 and 8 are each a cross-sectional view a portion of the left ventricle of the heart, illustrating the tether being moved to a second location and securing the tether with a new epicardial pad at a second location on the ventricular wall of the heart using an intraventricular snare device, according to an embodiment.

FIG. 9 illustrates an angle of the tether relative to the prosthetic mitral valve of FIG. 6 after being moved to the second location on the ventricular wall of the heart.

DETAILED DESCRIPTION

Figure 1:
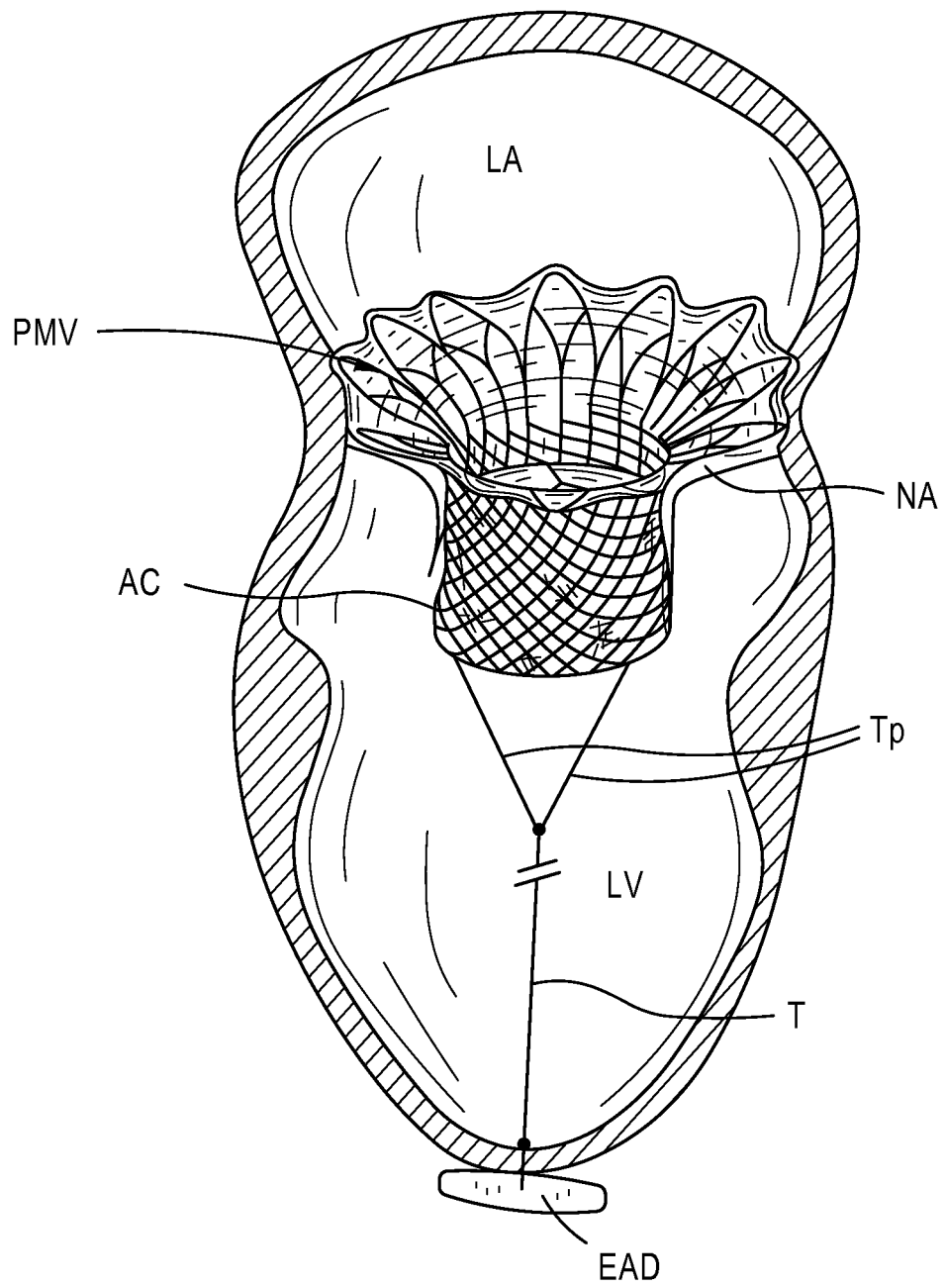
FIG. 1 is a cross-sectional illustration of a portion of a heart, including the left atrium and the left ventricle, with a prosthetic mitral valve implanted therein and an epicardial anchor device anchoring the mitral valve in position via a ventricular tether.

Apparatus and methods are described herein for repositioning or adjusting the anchoring location for an epicardial pad and tether that are used to secure or anchor a prosthetic valve within a heart, such as, for example, a prosthetic mitral valve or a prosthetic tricuspid valve. In some embodiments, an intraventricular snare device can be used to grab or snare the tether to move it to a new location. In some embodiments, an intraventricular catheter device can be used in which the tether can be threaded through the catheter device to move the tether to a new location.

In some embodiments, a method includes inserting a distal end portion of a snare device through an incision at a first location in a ventricular wall of a heart and within the left ventricle of the heart. A tether extending from a prosthetic mitral valve, through the left ventricle and out an incision at a second location on the ventricular wall of the heart is snared with the snare device. The tether is pulled with the snare device such that a proximal end of the tether is moved back through the incision at the second location on the ventricular wall and into the left ventricle. The snare device is pulled proximally such that the tether is pulled proximally through the incision at the first location in the ventricular wall of the heart.

In some embodiments, a method includes inserting a distal end portion of a catheter through an incision at a first location in a ventricular wall of a heart, through a left ventricle of the heart and through an incision at a second location in the ventricular wall while a proximal end of the catheter remains outside the incision at the first location, and such that a distal end portion of the catheter is disposed at least partially parallel to a tether extending through the incision at the second location in the ventricular wall. The tether is coupled at a distal end to a prosthetic mitral valve implanted within the heart. At least a portion of the tether is threaded through a lumen defined by the catheter until a proximal end of the tether extends out of a proximal end of the catheter outside of the heart. The catheter is pulled proximally such that the distal end portion of the catheter extends within the left ventricle of the heart with the tether extending through the lumen of the catheter outside of the heart. A tension on the tether between the prosthetic mitral valve and the incision at the first location in the ventricular wall of the heart can be adjusted.

In some embodiments, a method includes inserting a distal end of a catheter through an incision at a first location in a ventricular wall of a heart, through a left ventricle of the heart and through the ventricular septum of the heart such that the distal end of the catheter is disposed within the right ventricle. A portion of the catheter extends through the incision at the first location with the proximal end of the catheter disposed outside the heart. A snare device is moved distally within a lumen of the catheter until a distal end of the snare device is disposed within the right ventricle. A tether extending from a prosthetic tricuspid valve implanted within the heart, within the right ventricle and through an incision at a second location in the ventricular wall of the heart is snared with the snare device. The tether is pulled with the snare device through the lumen of the catheter such that the proximal end of the tether is pulled out the proximal end of the catheter outside of the heart.

In some embodiments, a method includes inserting a distal end of a catheter through an incision at a first location in a ventricular wall of a heart such that the distal end of the catheter is disposed within a left ventricle of the heart. A snare device is inserted through an incision at a second location in the ventricular wall of the heart such that a distal end portion of the snare device is disposed with the left ventricle of the heart. A tether extends from a prosthetic mitral valve, through the left ventricle out through the incision at the second location in the ventricular wall of the heart. The distal end portion of the catheter is snared with the snare device and the snare device is pulled, along with the snared distal end portion of the catheter, through the incision at the second location in the ventricular wall, while a proximal end of the catheter remains outside the incision at the first location. A distal end of the tether is threaded through a distal opening defined by the catheter, through a lumen defined by the catheter and out a proximal opening defined by the catheter. The catheter is removed, leaving the tether extending through the incision at the first location in the ventricular wall of the heart. A tension on the tether between the prosthetic mitral valve and the incision at the first location in the ventricular wall of the heart can be adjusted and the tether can be secured at the first location on the ventricular wall of the heart with an epicardial pad device.

In some embodiments, an adjustable tether and epicardial pad or anchor system for a transcatheter mitral valve replacement is described herein, and more particularly an apparatus and methods for adjustably securing and positioning a transcatheter prosthetic trtitral valve that has been deployed into the native tritral annulus. For example, the prosthetic mitral valve can be anatomically secured in a two-phase process which includes securing the valve in the native annulus using a cuff and tether axial tensioning system in combination with a lateral expanded stent tensioning system, and to methods for making such systems.

In some embodiments, an adjustable-tether and epicardial pad system for a compressible prosthetic heart valve replacement is described herein, which can be deployed into a closed beating heart using, for example, a transcatheter delivery system. In some embodiments, such an apparatus can be deployed via a minimally invasive fashion and by way of example considers a minimally invasive surgical procedure utilizing the intercostal or subxyphoid space for valve introduction. In order to accomplish this, the valve is formed in such a manner that it can be compressed to fit within a delivery system and secondarily ejected from the delivery system into the target location, for example, the mitral or tricuspid valve annulus.

In some embodiments, there is provided a method of tethering a prosthetic heart valve during a transcatheter valve replacement procedure that includes deploying a transcatheter prosthetic heart valve in a patient using as an anchor an adjustable tether that is anchored within the heart between an apically affixed epicardial fastening device and a stent-based fastening system. The transcatheter prosthetic heart valve can include an expandable tubular stent having a cuff and an expandable internal leaflet assembly. The cuff includes wire covered with stabilized tissue or synthetic material, and the leaflet assembly is disposed within the stent and includes stabilized tissue or synthetic material.

In another embodiment, a prosthetic heart valve can be tethered to the apex of the left ventricle using an interlocking tethering system that includes a stent-based component and an adjustable-tether distal component that cooperatively engages with the stent-based component to form a secure attachment of the prosthetic heart valve to the apex, and an adjustable-tether proximal component that attaches to an epicardial tether securing device.

In some embodiments, an epicardial anchor device for anchoring a transluminal (transventricular) suture/tether includes a substantially rigid suturing disk having a tether-capture mechanism such as an axial tunnel, a winding channel, or a functional equivalent, and a tether locking mechanism such as a locking pin or screw that intersects the axial tunnel, a locking pin or screw operatively associated with the winding channel, a cam device like a rope lock that grips the tether by compression between two cams or a cam and fixed locking wall, a metal compression fastener, a tooth and pawl device, various combinations of the above, or a functional equivalent thereof.

In another embodiment, an epicardial anchor device for anchoring a transluminal suture includes a substantially rigid suturing disk having an axial tunnel, a locking pin tunnel that intersects the axial tunnel, a locking pin operatively associated with the locking pin tunnel, one or more radial channels that do not intersect with the axial tunnel and that do not intersect the locking pin tunnel, and a winding channel circumferentially disposed within a perimeter sidewall of the disk.

In some embodiments, an epicardial anchor device further includes a polyester velour coating. In some embodiments, the one or more radial channels includes four radial channels. In some embodiments, the one or more radial channels each have an enlarged axial keyhole tunnel.

In some embodiments, an epicardial anchor device includes a flexible pad operatively associated with the rigid tethering/suturing disk, and the flexible pad has a through-hole longitudinally aligned with the axial tunnel In some embodiments, the epicardial anchor device further includes a sleeve gasket operatively associated with the rigid tethering/suturing disk, and the sleeve gasket has a lumen longitudinally aligned with the axial tunnel In some embodiments, the device further includes a sleeve gasket attached to the rigid tethering/suturing disk and a flexible pad attached to the sleeve gasket. In such an embodiment, the sleeve gasket has a lumen longitudinally aligned with the axial tunnel of the tethering/suturing disk, and the flexible pad has a through-hole longitudinally aligned with both the lumen of the sleeve gasket and the axial tunnel of the tethering/suturing disk.

In some embodiments, a device for anchoring a transluminal tethering/suture includes a substantially rigid tethering/suturing disk, a sleeve gasket connected to the tethering/suturing disk, and a flexible pad connected to the sleeve gasket. The substantially rigid tethering/suturing disk has an axial tunnel, a locking pin tunnel that intersects the axial tunnel, a locking pin operatively associated with the locking pin tunnel, one or more radial channels that do not intersect with the axial tunnel and that do not intersect the locking pin tunnel, and a winding channel circumferentially disposed within a perimeter sidewall of the disk. The sleeve gasket is in longitudinal alignment with the axial tunnel, and the flexible pad has a through-hole longitudinally aligned with both the lumen of the sleeve gasket and the axial tunnel of the tethering/suturing disk.

In another embodiment, an epicardial anchor device for anchoring a transluminal suture includes a substantially rigid tethering/suturing disk having an axial tunnel, a locking pin tunnel that intersects the axial tunnel, and a locking pin operatively associated with the locking pin tunnel In some embodiments, a method for anchoring a transluminal suture includes affixing a transluminal suture to an epicardial anchor device, and positioning the epicardial anchor device external to a body lumen. The transluminal tether/suture extends from within the lumen to the epicardial anchor device.

In another embodiment, a tether and epicardial anchor device as described herein further includes at least one tether tension meter, tether tension gauge, or tether tension load measuring device operatively associated with the tether. In some embodiments, a tension sensor includes an electronic strain gage transducer. The tension sensor can be configured for dynamic tension, static tension, or both dynamic and static tension measurement. In some embodiments, the tension meter includes internal rollers that engage the tether. In some embodiments, the tether is loaded with a specific tension, such as 1.0-4.0 lbs.

In some embodiments, a sterile surgical kit is provided. The sterile surgical kit can contain a transcatheter delivery system, an epicardial anchor device and/or a transcatheter prosthetic valve.

In another embodiment, there is provided method of treating mitral or tricuspid regurgitation in a patient, which includes surgically deploying an adjustable-tethered prosthetic heart valve into the mitral or tricuspid annulus of the patient.

In another embodiment, the space between the cuff tissue and cuff Dacron liner (inside-outside) may be used to create a cuff that is expandable, swellable or may be inflated, and which provides an enhanced level of sealing of the cuff against the atrial trabeculations and annular tissue.

In some embodiments described herein, a tethering system for a prosthetic mitral valve is provided that is designed to maintain integrity to about 800 million cycles, or about 20 years. The use of a compressible prosthetic valve delivered via transcatheter endoscope techniques addresses various delivery issues. Deployment is addressed through the use of a prosthetic valve having a shape that features a tubular stent body that contains leaflets and an atrial cuff. This allows the valve to seat within the mitral annulus and be held by the native mitral leaflets. The use of a flexible valve attached using an apical tether provides compliance with the motion and geometry of the heart. The geometry and motion of the heart are well-known as exhibiting a complicated biphasic left ventricular deformation with muscle thickening and a sequential twisting motion. The additional use of the apically secured ventricular tether helps maintain the prosthetic valve's annular position without allowing the valve to migrate, while providing enough tension between the cuff and the atrial trabeculations to reduce and eliminate perivalvular leaking. The use of an adjustable tether or an adjustable paired-tether that is attached to an apical location can reduce or eliminate the cardiac muscle remodeling that has been witnessed in prior art devices. Some prior art devices can have a problem with unwanted change in tissue at the anchoring locations, as well as heart-generated migration of the original anchoring locations to new locations that reduce or destroy the prior art valve's effectiveness. The use of a compliant valve prosthesis and the special shape and features help reduce or eliminate clotting and hemodynamic issues, including left ventricular outflow tract (LVOT) interference problems. Many prior art valves were not even aware of or were not able to address problems with blood flow and aorta/aortic valve compression issues.

Structurally, a prosthetic heart valve as used with the apparatus and methods described herein can be a self-expanding tubular stent having a cuff at one end and tether loops for attaching tethers at the other end. Disposed within the tubular stent is a leaflet assembly that contains the valve leaflets, and the valve leaflets can be formed from stabilized tissue or other suitable biological or synthetic material. In one embodiment, the leaflet assembly may even include a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

The upper cuff portion may be formed by heat-forming a portion of a tubular Nitinol® braided (or similar) stent such that the lower portion retains the tubular shape, but the upper portion is opened out of the tubular shape and expanded to create a widened collar structure that may be shaped in a variety of functional regular or irregular funnel-like or collar-like shapes. In one embodiment, the entire structure is formed from a laser-cut stent and collar design, as described further herein As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

A prosthetic mitral valve can be anchored to the heart at a location external to the heart via one or more tethers coupled to an anchor device, as described herein. For example, the tether(s) can be coupled to the prosthetic mitral valve and extend out of the heart and be secured at an exterior location (e.g., the epicardial surface) with an anchor device, as described herein. An anchor device as described herein can be used with one or more such tethers in other surgical situations where such a tether may be desired to extend from an intraluminal cavity to an external anchoring site. Various different types and/or configurations of an anchor device (also referred to herein as "epicardial anchor device" or "epicardial pad" or "pad") can be used to anchor a prosthetic mitral valve in the methods described herein. For example any of the epicardial anchor devices described in the '218 PCT application incorporated by reference above can be used.

FIG. 1 is a cross-sectional illustration of the left ventricle LV and left atrium LA of a heart having a transcatheter prosthetic mitral valve PMV deployed therein and an epicardial anchor device EAD as described herein securing the prosthetic mitral valve PMV in place. FIG. 1 illustrates the prosthetic mitral valve PMV seated into the native valve annulus and held there using an atrial cuff AC of the prosthetic mitral valve PMV, the radial tension from the native leaflets, and a ventricular tether T secured with attachment portions Tp to the prosthetic mitral valve PMV and to the epicardial anchor EAD. The epicardial anchor device EAD can be various different shapes, sizes, types and configurations, for example, the EAD can be an epicardial anchor device such as those described in the '218 PCT application incorporated by reference above. Further, the prosthetic mitral valve PMV and the tether T can be, for example, a prosthetic mitral valve and tether, respectively, as described in the '218 PCT application or other suitable types and configurations.

Figure 2:
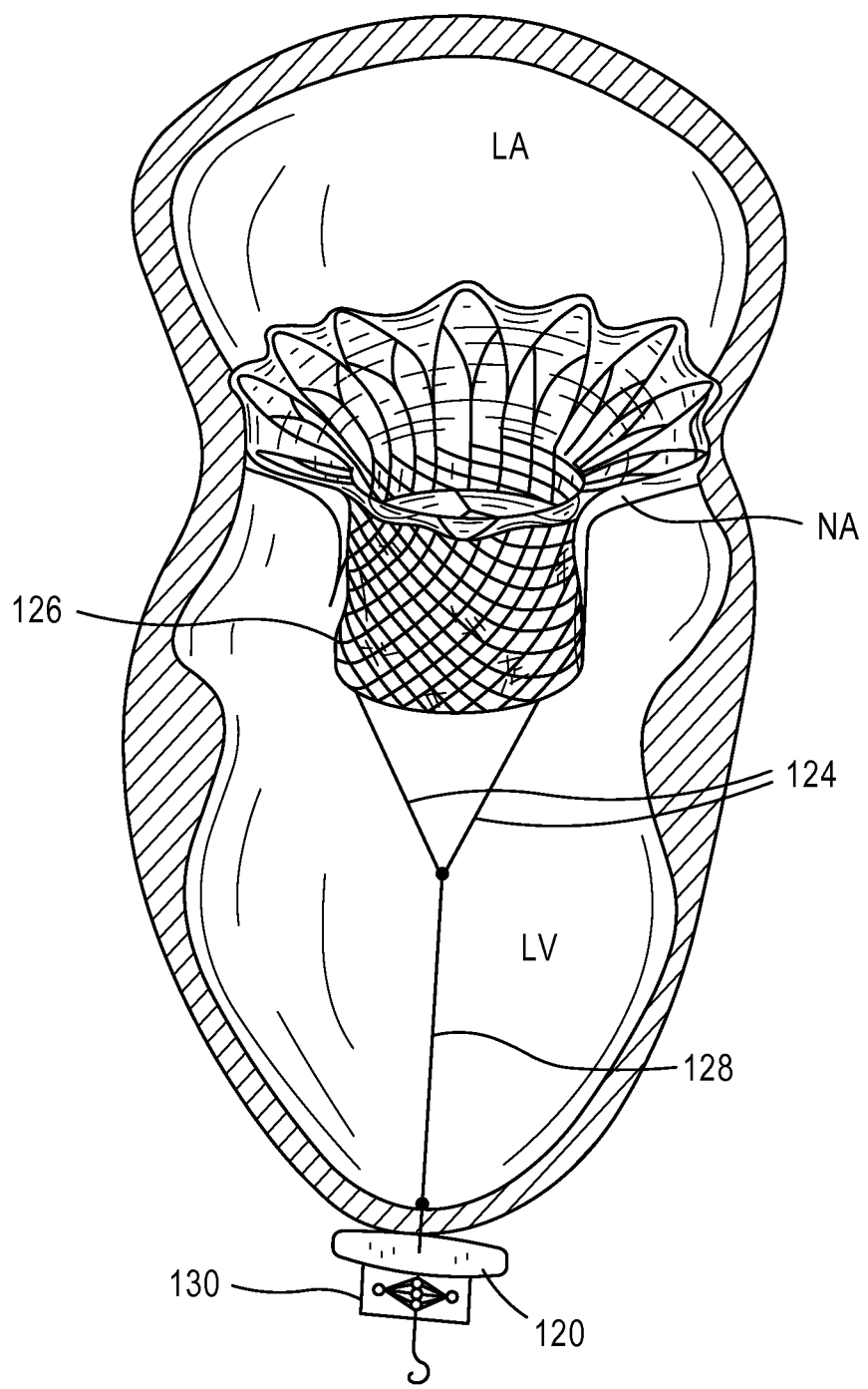
FIG. 2 is a cross-sectional illustration of a portion of a heart, including the left atrium and the left ventricle, with a prosthetic mitral valve implanted therein with a ventricular tether secured by an epicardial anchor, and an adjustment and tensioning element operatively associated with the epicardial anchor.

FIG. 2 is a cross-sectional illustration of the left ventricle LV and left atrium LA of a heart having a transcatheter prosthetic mitral valve 126 deployed therein and an epicardial anchor device 120 securing the prosthetic mitral valve 120 in place. As described above for FIG. 1, the prosthetic mitral valve 126 is seated into the native annulus NA and held there using an atrial cuff, the radial tension from the native leaflets, and a single ventricular tether 128 secured by the epicardial anchor device 120 to the apex of the heart. The tether 128 includes tether portions 124 that are attached to the prosthetic mitral valve 126. In this embodiment, an epicardial adjustment and tensioning element 130 (also referred to herein as "tensioning element" or "tensioning member") is operatively associated with the epicardial anchor device 120 and attached to the tether 128. The tensioning element 130 can include, for example, at least one tether tension meter, tether tension gauge, or tether tension load measuring device operatively associated with the tether 128. A tension sensor can include, for example, an electronic strain gage transducer. The tension sensor can be designed for dynamic tension, static tension, or both dynamic and static tension measurement. A tension meter may include a load cell transducer, tension sensor with internal rollers that engage the tether, or similar tension meter known in the art. Example embodiments of a tension meter are described below with reference to FIGS. 4 and 5.

Figure 3:
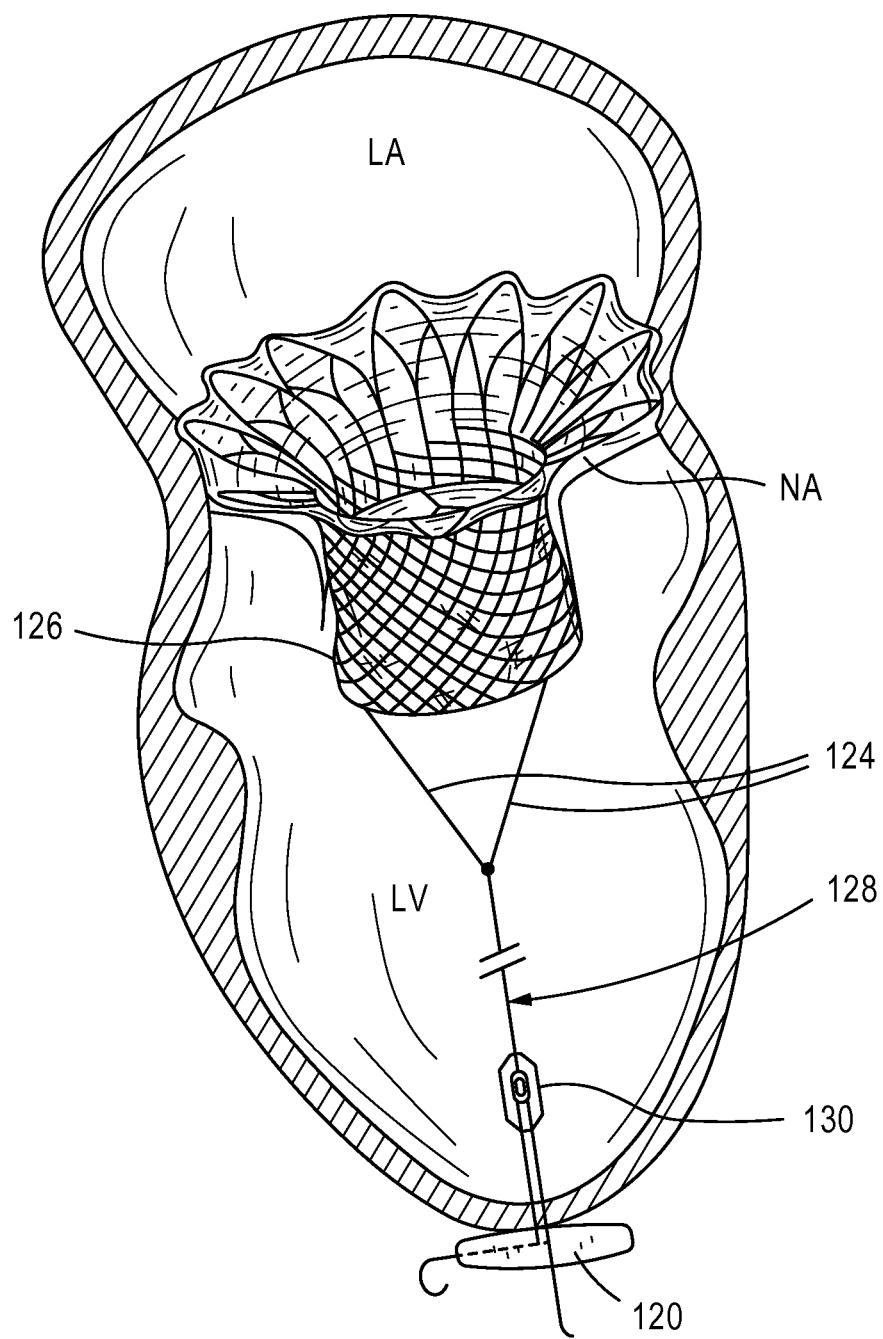
FIG. 3 is a cross-sectional illustration of portion of a heart, including the left atrium and the left ventricle, with a prosthetic mitral valve implanted therein with a ventricular tether secured by an epicardial anchor, and an intra-ventricular adjustment and tensioning element coupled to the tether.

FIG. 3 is a cross-sectional illustration of the left ventricle LV and left atrium LA of a heart with the transcatheter prosthetic mitral valve 126 deployed therein as described above, and an epicardial anchor device 120 securing the prosthetic mitral valve 120 in place. In this embodiment, a tensioning element 130 is disposed intra-ventricularly and attached to the tether 128.

Figure 4:
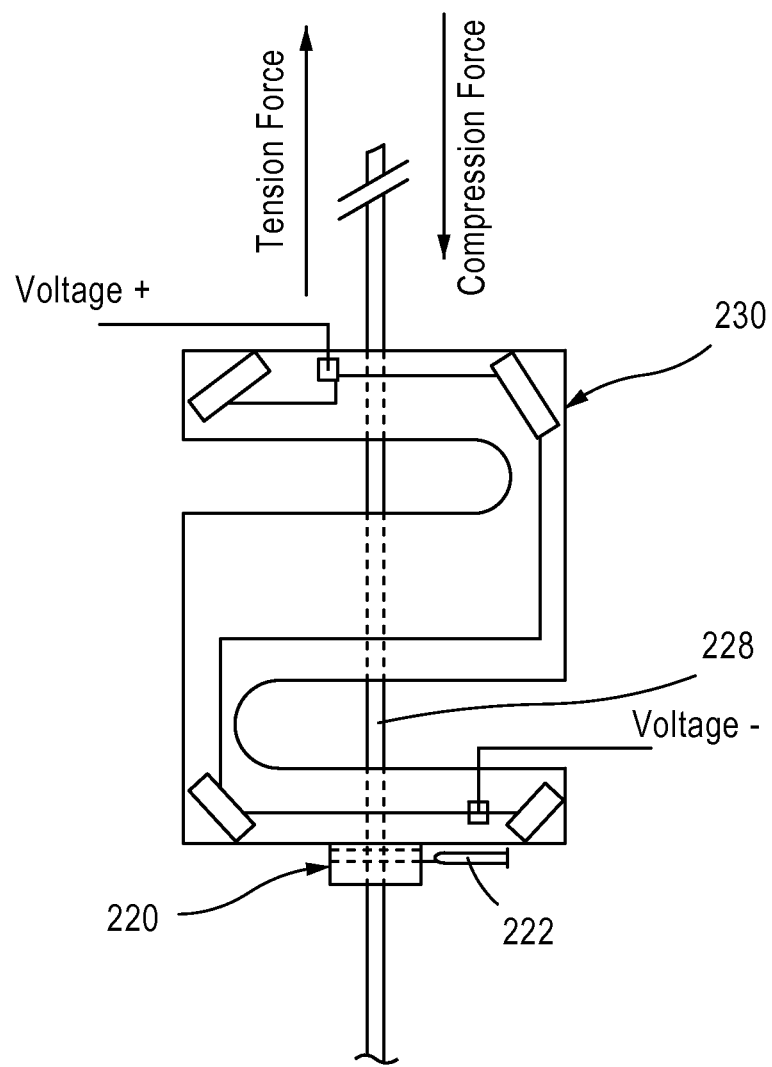
FIG. 4 is a side view of an embodiment of an S-shaped load element for use in a tension gauge.

FIG. 4 shows an example of one embodiment of an epicardial adjustment and tensioning device 230 that can be used to measure and adjust the load or tension on a tether attached to a prosthetic mitral valve (not shown in FIG. 4) and an epicardial anchor device, described herein. In this embodiment, the tensioning device 230 is in the form of a load cell transducer. As shown in FIG. 4, the load cell transducer tensioning device 230 can be coupled to a tether 228 extending from a prosthetic valve (not shown) and attached to an epicardial anchor device 220. In this embodiment, the anchor device 220 includes a pin 222 that can be inserted through an opening in the anchor device 220 to pierce the tether 228 and secure the tether to the anchor device 220. The load cell transducer tensioning device 230 can be made from a machined metal spring element such that when compression or tension forces are applied to the spring element, a strain is placed on the metal. Strain gauges are affixed to the metal spring element such that when stain forces increase or decrease on the spring element, the electrical circuit formed by the gauges captures the change in resistance that corresponds to the amount of strain. When voltage is applied to one side of the spring element, the opposite side will transmit an output voltage, and when strain forces are applied, the change in voltage can be measured.

Figure 5:
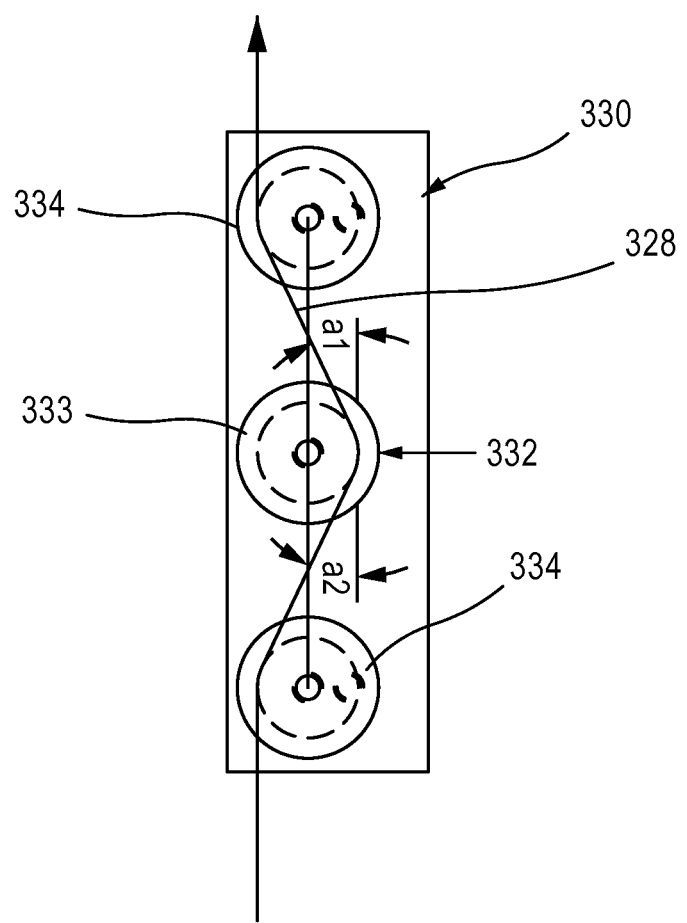
FIG. 5 is a side view of an embodiment of a roller-type load element for use in a tension gauge.

FIG. 5 illustrates an embodiment of another type of epicardial adjustment and tensioning device 330. The tensioning device 330 is in the form of a tension meter that can be coupled to a tether 328 attached to a prosthetic mitral valve (not shown in FIG. 5) and an epicardial anchor device (not shown in FIG. 5), described herein. The tension meter tensioning device 330 can include a roller-type load element 332 for use in exerting a tension on the tether 328. One or more strain gauge sensors (not shown) can be operatively coupled to the load element 332, and used to measure the displacement force on the middle or sensor roller 333, or to measure a change of angle as converted to the roller axis, or both. The physical tension can be converted to an electric signal to monitor the change in tension of a tether 328 which is operatively connected thereto. Using this tension meter 330, the tether 328 is fed through a pathway that includes a section that contacts the middle or sensor roller 333, and is fed over the sensor roller 333. This sensor roller 333 is usually placed between two fixed rollers 334 such that the tether 328 zig-zags through the set of rollers. This path creates a deflection angle relative to the axis of the tether on each end of the tensioning device 330. When the tether 328 moves, the sensor roller 333 either revolves, changing the angle of incidence from the fixed roller on either side, or the roller 333 itself is subjected to an orthogonal force vector, which (roller force) can be measured using a voltage change technique. In some embodiments, the tether 328 can be loaded with a specific tension, such as 1.0-4.0 lbs.

Figure 6:
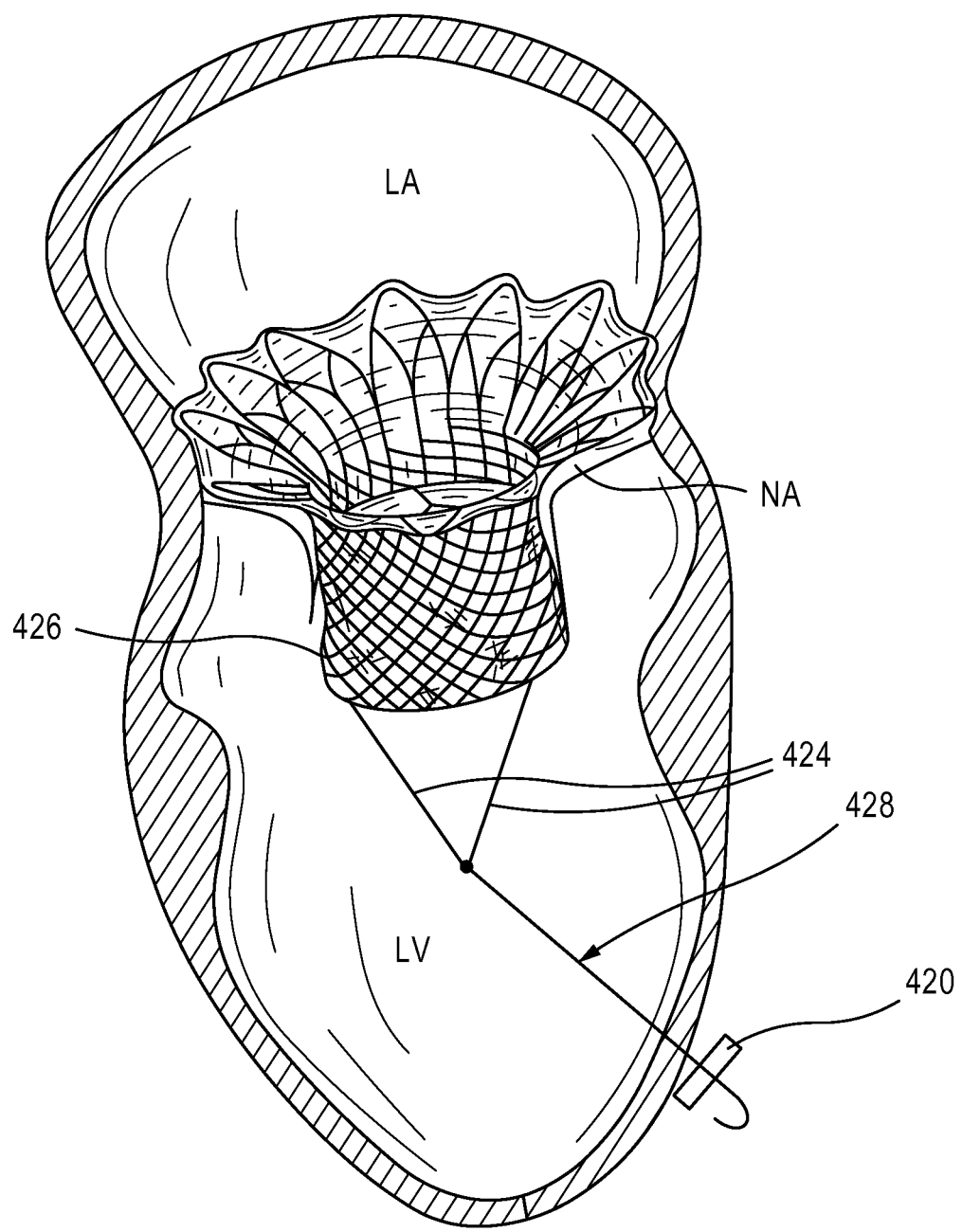
FIG. 6 is a cross-sectional view of a portion of a heart, including the left atrium and the left ventricle, with a prosthetic mitral valve implanted therein and an epicardial anchor device anchoring the prosthetic mitral valve via a tether in a first location on a ventricular wall the heart.

FIG. 6 illustrates a deployed prosthetic mitral valve 426 with an attached tether 428 that is anchored at an initial or first off-center position on the ventricular wall of the heart with an epicardial anchor device 420. The tether 428 includes tether portions 426 that couple the tether 428 to the prosthetic mitral valve 426. After the initial anchoring of the tether 428 at the first position, it may be desirable to move the tether 428 to a different desired anchored position on the ventricular wall. For example, after the initial placement of the prosthetic valve 426, it may be desirable to move the anchor location of the tether 428 to correct or improve the positioning of the deployed prosthetic mitral valve 426. For example, the initial placement of the prosthetic mitral valve 426 may provide an undesirable or less than optimal annulus-to-anchor pad angular relationship. In some cases, the tether may have been erroneously misaligned during the deployment process or the misalignment can arise from post-deployment migration of the tether due to, for example, anatomical reconfiguration or remodeling of the heart.

As shown in FIG. 7, a snare device 440 can be used to snare or capture the tether 428 and pull it back into the left ventricle and out through the ventricular wall at a different location, such as at the apex of the heart. A procedure catheter 442 can be used to introduce the snare device 440 into the heart. When repositioning the tether 428, a new epicardial anchor device 420' can be used to secure the tether 428 at the new or second location. As shown in FIG. 8, the tether 428 is repositioned at the new location and secured to the ventricular wall with the epicardial anchor device 420'. In this new location, the angular position between the tether 428 and the mitral annulus can be placed at a more desired angular position such as, for example, 90 degrees as shown in FIG. 8 and shown schematically in FIG. 9. FIG. 9 illustrates the angle a between the commissural-commissural (CC) plane/axis P1 of the mitral annulus and the tether 428. The apical lateral plane/axis P2 is associated with the location of the epicardial anchor device 420'. The angle a can be for example, 90 degrees or substantially 90 degrees or a different desired angle.

Figure 10:
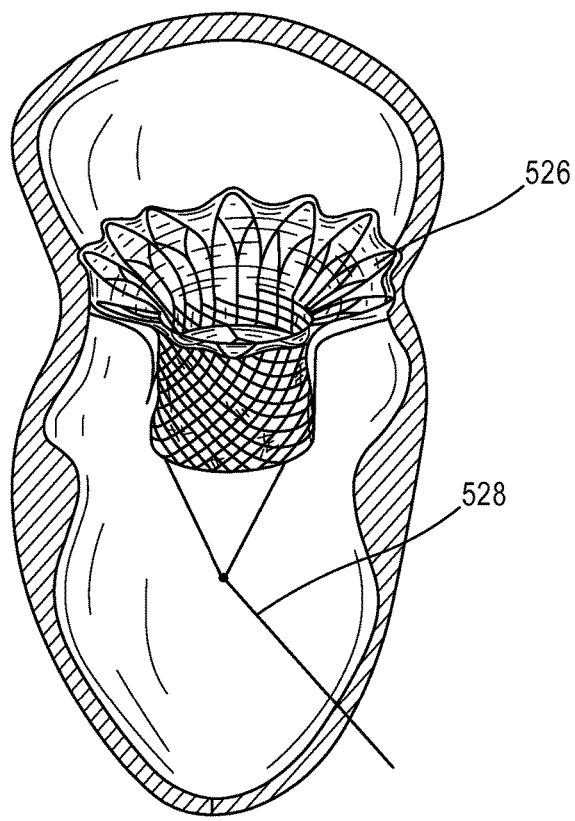
FIG. 10 is a cross-sectional view a portion of a heart, including the left atrium and the left ventricle, with a prosthetic mitral valve implanted therein and an epicardial anchor device anchoring the prosthetic mitral valve via a tether in a first location on a ventricular wall the heart.
Figure 11:
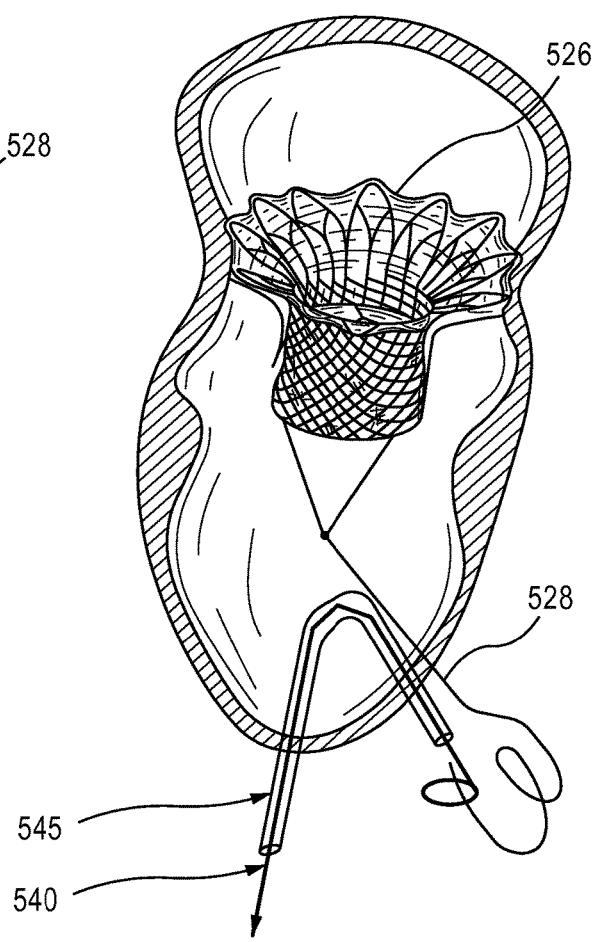
FIGS. 11-14 are each a cross-sectional view a portion of the left ventricle of the heart, illustrating the tether of FIG. 10 being moved and secured with a new epicardial pad at a second location on the ventricular wall of the heart using an intraventricular catheter device, according to an embodiment.
Figures 12, 13:
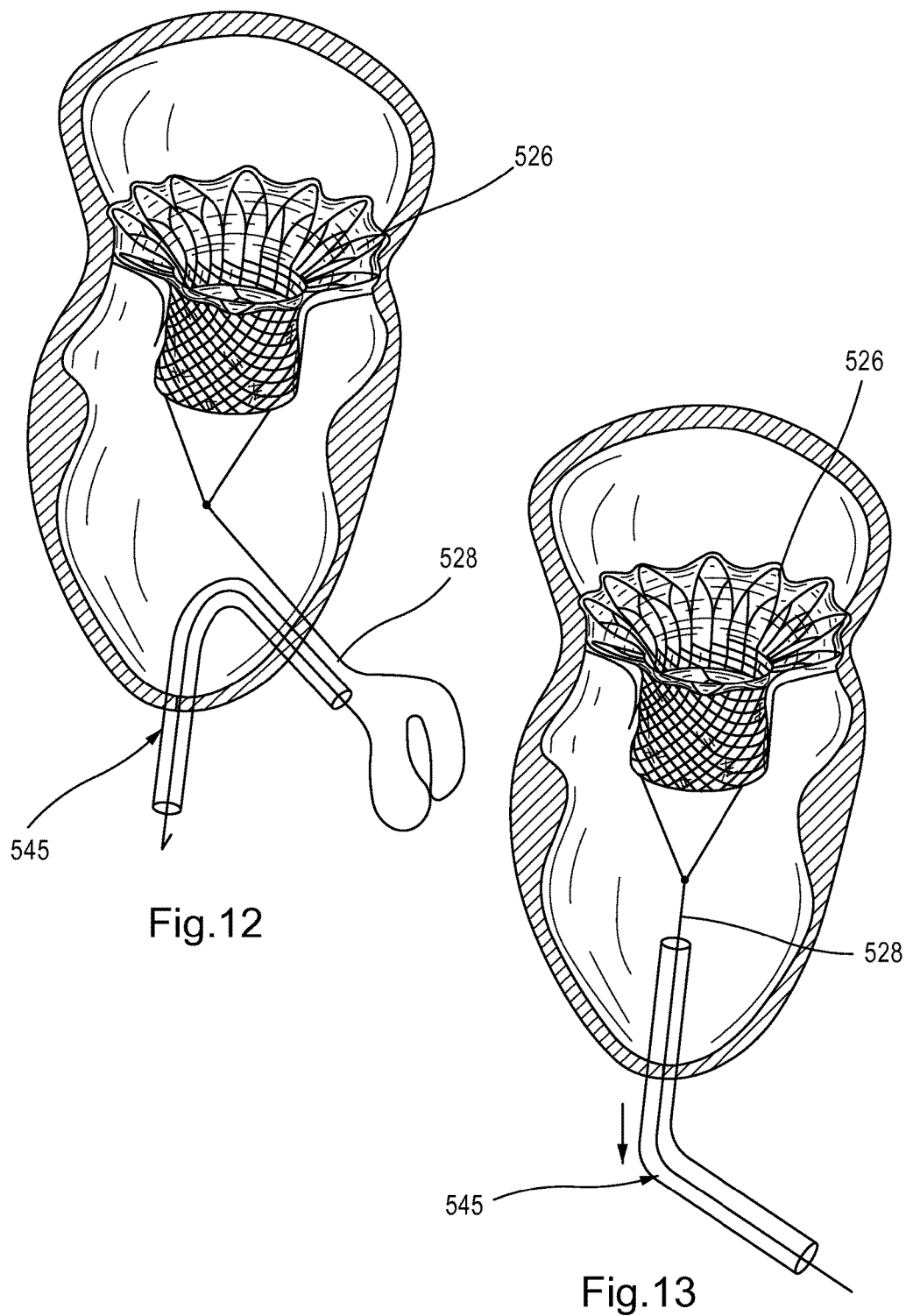

FIG. 10 illustrates another embodiment of a deployed prosthetic mitral valve 526 with an attached tether 528 that is anchored at an initial or first off-center position on the ventricular wall of the heart. Although not shown, the tether 528 can be secured to the ventricular wall with an epicardial anchor device as described above. As with the previous embodiment, after the initial positioning or anchoring of the tether 528 at the first position, it may be desirable to move the tether 528 to a different desired anchored position. In this embodiment, an intraventricular catheter 545 and snare device 540 can be used to capture the deployed tether 528 and move it to a new location as shown in FIGS. 11-13.

Figure 14:
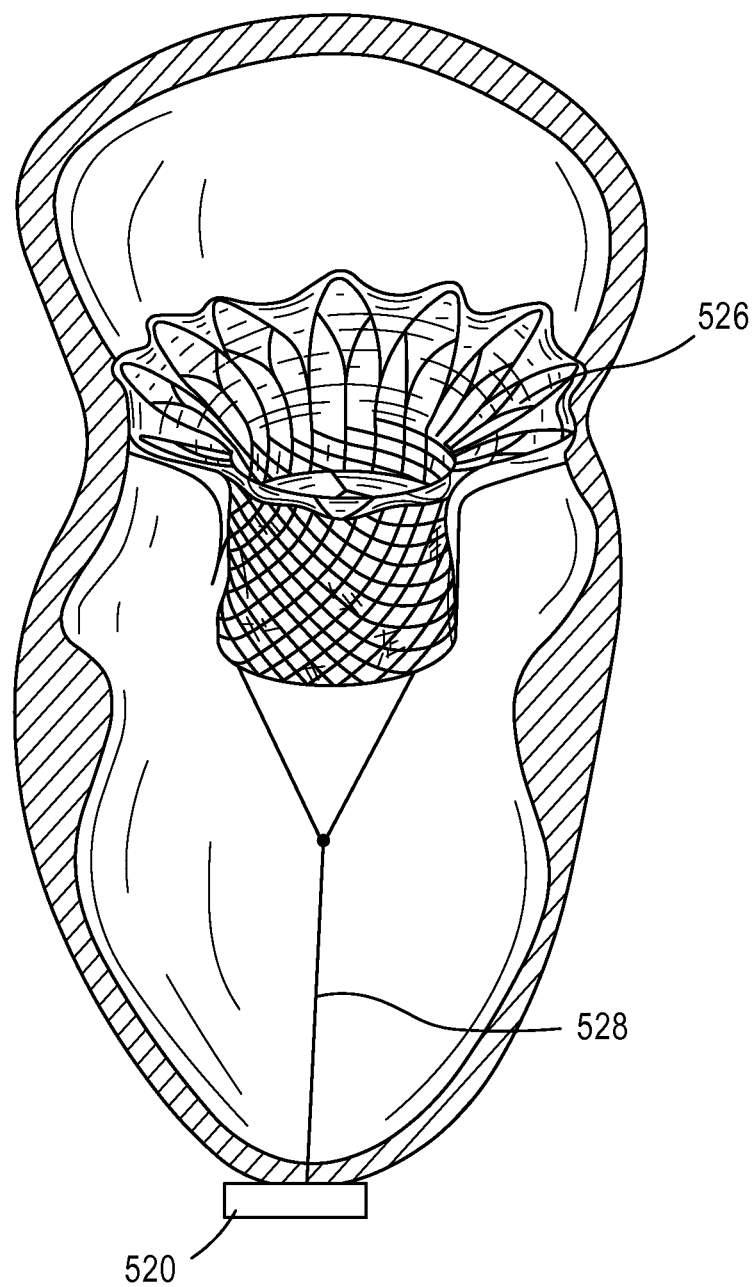

The catheter 545 can be flexible and/or steerable and/or can be formed with bends or curves specifically configured for such use. The catheter 545 can be inserted into the left ventricle at a desired improved or corrected position. The catheter 545 can then be directed to exit the ventricle through the same aperture (perforation) in which the tether 528 extends out of the heart. In this manner, both the tether 528 and the catheter 545 exit the ventricle in parallel. The tether 528 can be manually fed through the catheter 545 or as shown in FIG. 11, the snare 540 can be inserted through the catheter 545 and used to capture and pull the tether 528. The tether 528 is pulled into the catheter 545 and through the catheter 545 at the new desired anchor position at or near the apex of the heart as shown in FIG. 12. The catheter 545 can then be withdrawn, and the tether 528 pulled proximally such that the tether 528 is pulled to a desired tension at the new second anchor position as shown in FIG. 13. The initial perforation at the first anchor location can be closed with sutures using known techniques, and the tether 528, at its new position, can be anchored in place with, for example, an epicardial pad device 520 as shown in FIG. 14. Alternatively, other anchoring methods can be used, such as tying the tether 528, or using a clip or other suitable device.

Figure 15:
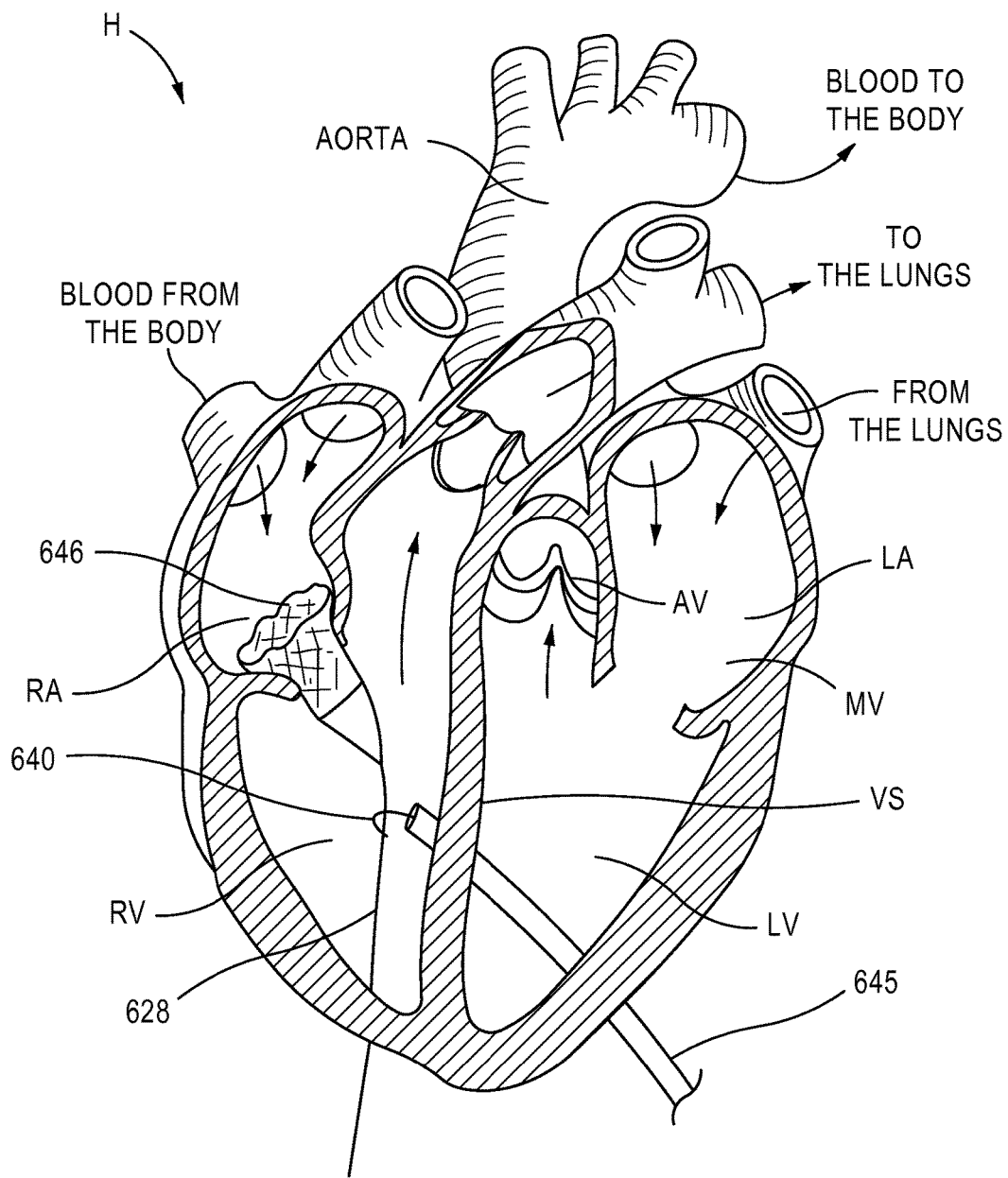
FIGS. 15 and 16 are each a cross-sectional view a portion of a heart, including the left atrium, the left ventricle, the right atrium and the right ventricle, with a prosthetic tricuspid heart valve implanted within the right atrium, and illustrating a method of anchoring the prosthetic valve via a tether and epicardial anchor device, according to an embodiment.
Figure 16:
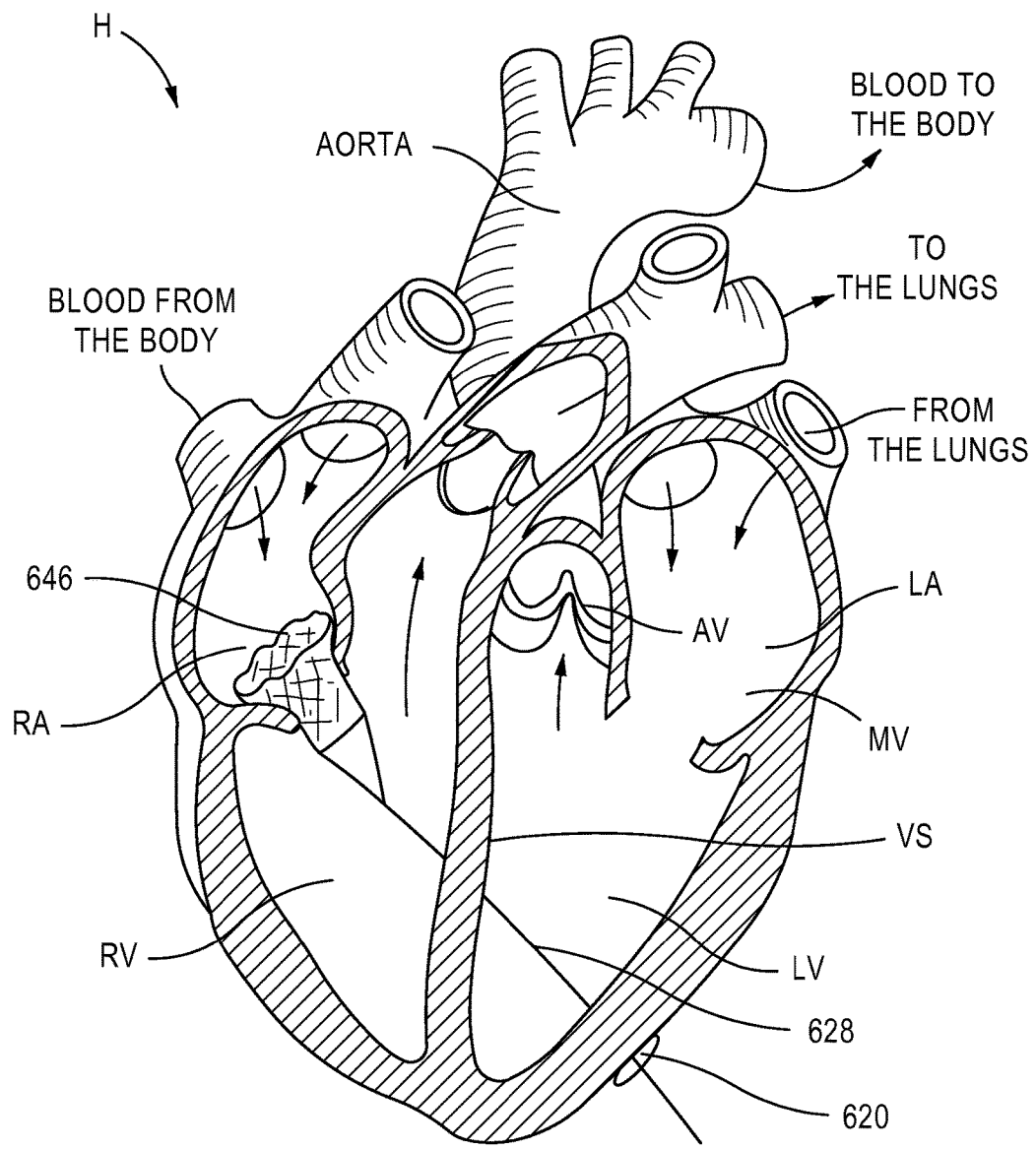

In the embodiments described above, the prosthetic valve is a prosthetic mitral valve and the tether extends downward through the left ventricle, exiting the left ventricle at the apex of the heart to be fastened on the epicardial surface outside of the heart. Similar anchoring is contemplated herein as it regards to the tricuspid, or other valve structure requiring a prosthetic. For example, FIGS. 15 and 16 illustrate a prosthetic tricuspid heart valve implanted within the right atrium of the heart and the prosthetic tricuspid valve is initially anchored via a tether on a ventricular wall of the right ventricle. It may be desirable to move the anchor location for the tether to a wall of the left ventricle.

As shown in FIG. 15, a prosthetic tricuspid heart valve 646 is implanted within the right atrium of the heart, and a tether 628 extends from the tricuspid heart valve 646 and out an incision on the right ventricular wall. To move the tether 628 to a new anchor location, a catheter 645 and snare device 640 can be used in a similar manner as described above for the previous embodiment. The catheter 645 can be inserted through the wall of the left ventricle at a desired anchor location and inserted through the ventricular septum VS as shown in FIG. 15. The snare 640 can be movably disposed within a lumen of the catheter 645 and used to grab or snare the tether 628 within the right ventricle. The snare 640 can be moved proximally through the catheter 645 such that the tether 628 extends outside of the new anchor location on the wall of the left ventricle. The catheter 645 can then be removed leaving the tether 628 extending through the ventricular septum Sp, through the left ventricle LV and out the new anchor location as shown in FIG. 16. The tether 628 can be secured with an epicardial anchor device 620, or other securing methods or devices can be used.

Figure 17:
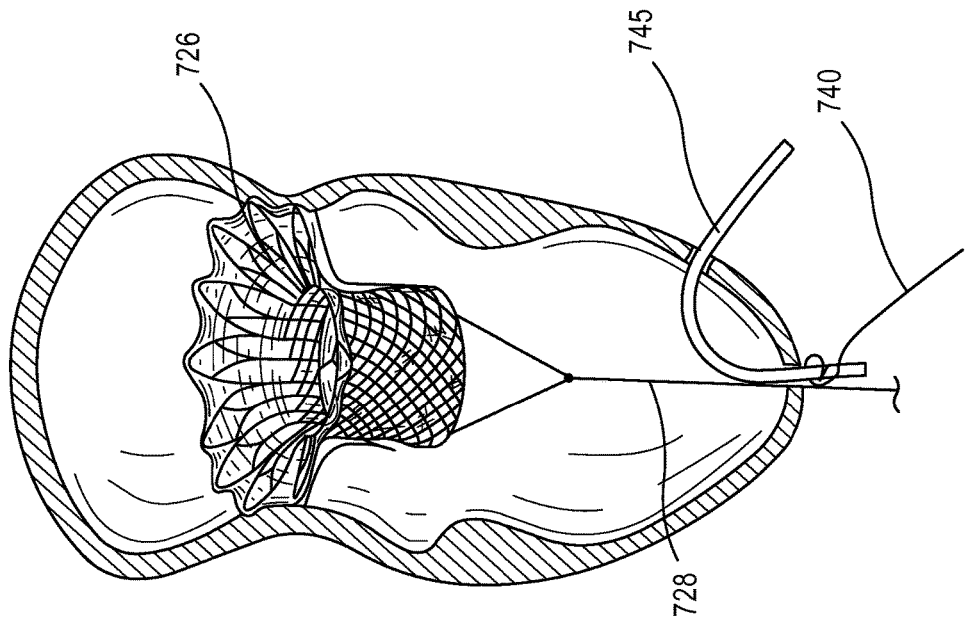
FIG. 17 is a cross-sectional view a portion of a heart, including the left atrium and the left ventricle, with a prosthetic mitral valve implanted therein and an epicardial anchor device anchoring the prosthetic mitral valve via a tether in a first location on a ventricular wall the heart.
Figure 18:
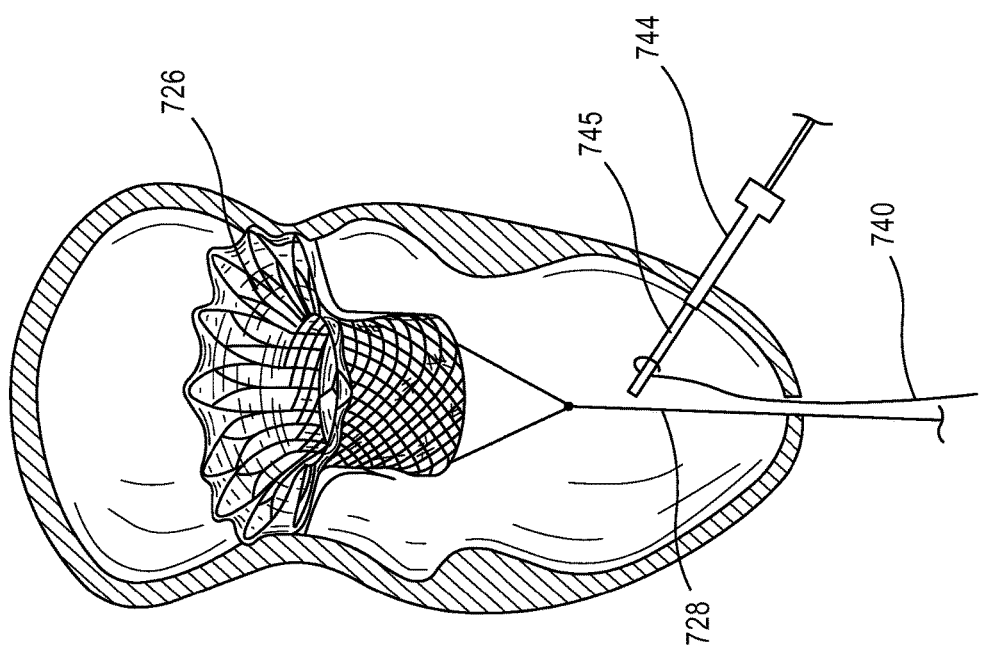
FIGS. 18-20 are each a cross-sectional view a portion of the left ventricle of the heart, illustrating the tether of FIG. 17 being moved and secured with a new epicardial pad at a second location on the ventricular wall of the heart using an intraventricular catheter device, according to an embodiment.

FIG. 17 illustrates another embodiment of a deployed prosthetic mitral valve 726 with an attached tether 728 that is anchored at an initial or first position on the ventricular wall of the heart. Although not shown, the tether 728 can be secured to the ventricular wall with an epicardial anchor device as described above. As with the previous embodiments, after the initial positioning or anchoring of the tether 728 at the first position, it may be desirable to move the tether 728 to a different desired anchored position. In this embodiment, an intraventricular needle 744, intraventricular microcatheter 745 and snare device 740 can be used to move the deployed tether 728 to a new location as shown in FIGS. 18-20.

As with previous embodiments, the microcatheter 745 can be flexible and/or steerable and/or can be formed with bends or curves specifically configured for such use. As shown in FIG. 17, the microcatheter 745 can be inserted e via the needle 744 through the ventricular wall of the heart at a desired improved or corrected position to anchor the tether 728 such that a distal end portion of the microcatheter is disposed within the left ventricle. Also shown in FIG. 17, in this embodiment, the snare device 740 is inserted through an opening in the heart in which the tether 728 extends out of the heart at the first position on the ventricular wall. The snare device 744 can be used to snare the distal end portion of the microcatheter 745 and pull the distal end portion of the microcatheter out through the heart at the opening in the ventricular wall in which the tether 728 extends at the first anchor position as shown in FIG. 18. The microcatheter 745 will then be extending between the first anchor position and the second desired anchor position in the ventricular wall of the heart. The needle 744 can be removed before or after the microcatheter 745 is pulled through the first anchor position.

Figure 19:
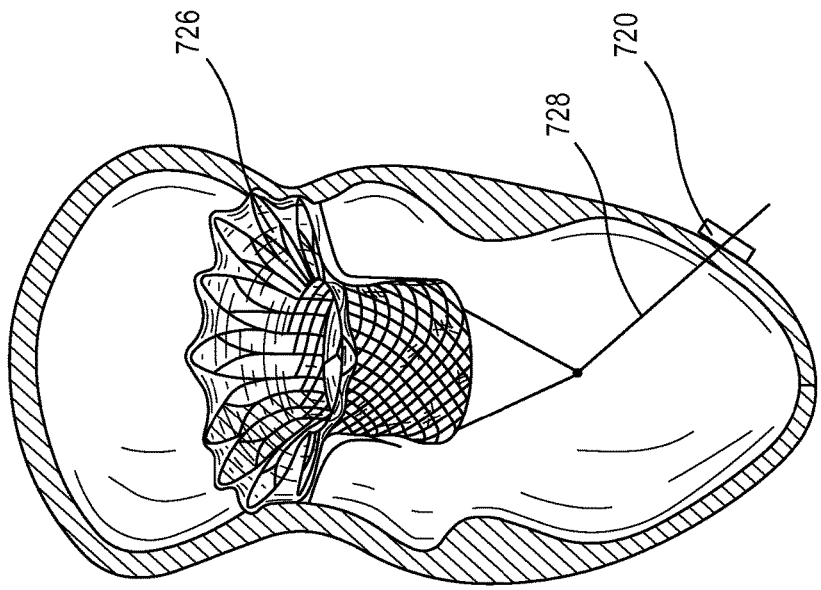
Figure 20:
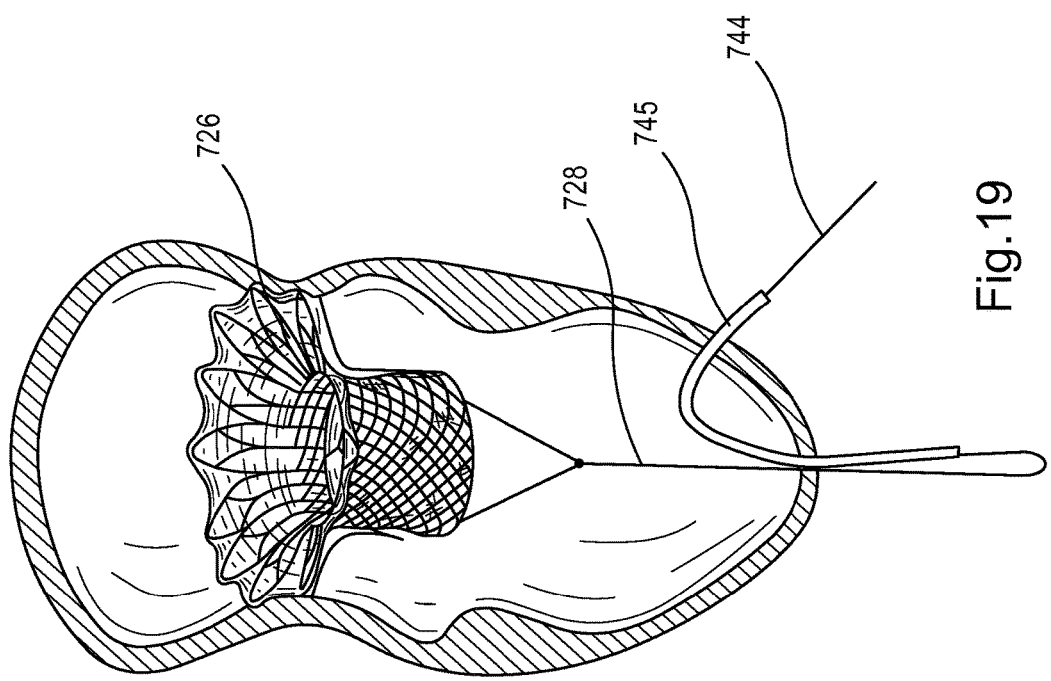

The proximal end of the tether 728 can then be manually threaded through the distal end opening of the microcatheter, through the lumen of the microcatheter and out through the proximal end opening of the microcatheter 745 as shown in FIG. 19. The microcatheter 745 can then be removed, leaving the tether 728 extending out of the heart at the second desired anchor location in the ventricular wall as shown in FIG. 20. Before or after the microcatheter is removed, the tether 728 can be pulled proximally such that the tether 728 is pulled to a desired tension at the new second anchor position as shown in FIG. 20. The initial perforation or opening at the first anchor location can be closed with sutures using known techniques, and the tether 728, at its new position, can be anchored in place with, for example, an epicardial pad device 720 as shown in FIG. 20. Alternatively, other anchoring methods can be used, such as tying the tether 728, or using a clip or other suitable device as described above for previous embodiments.

Figure 21:
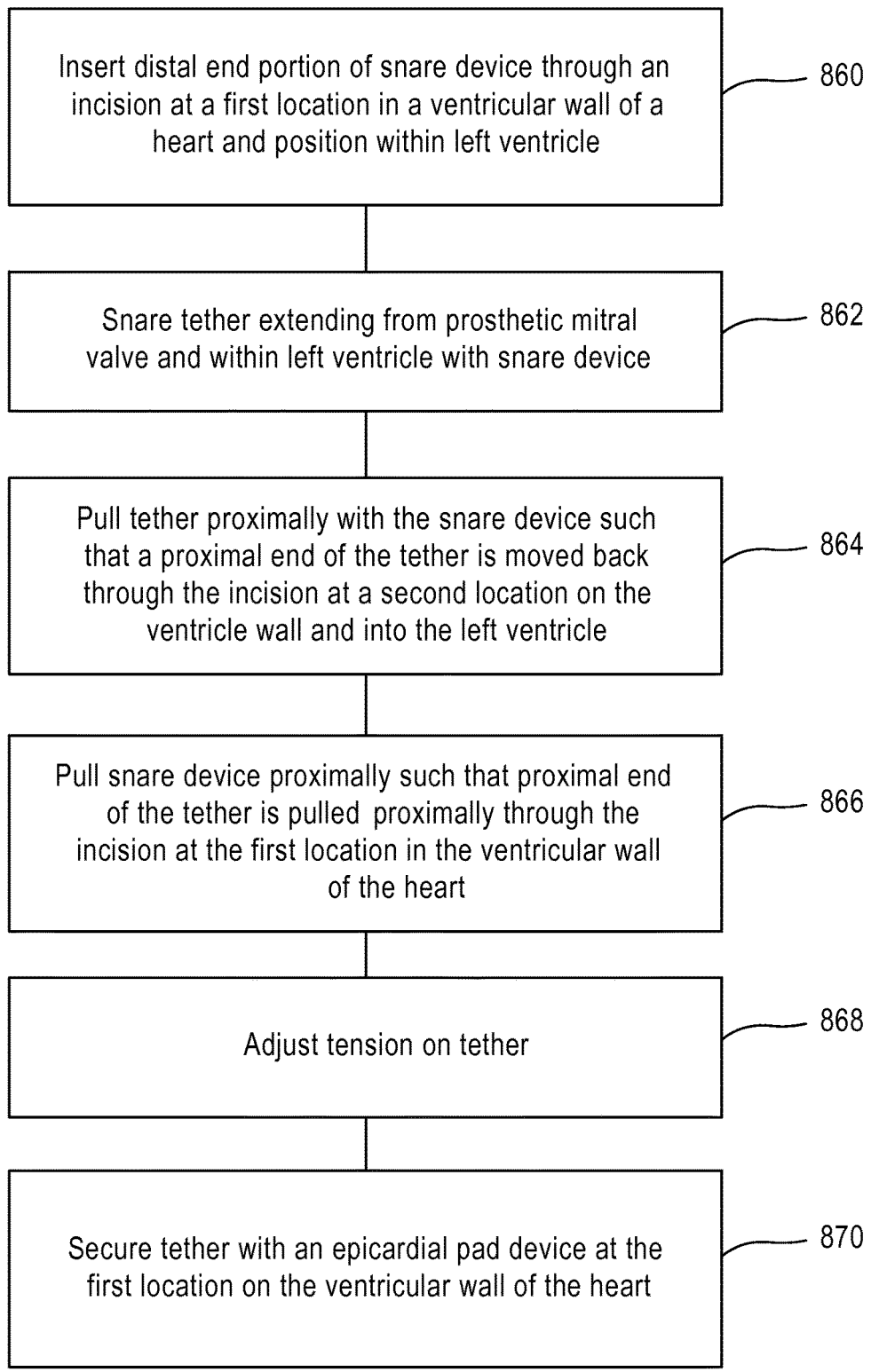
FIGS. 21-23 are each a flowchart illustrating a method of repositioning a tether to secure a prosthetic heart valve.

FIG. 21 is a flowchart illustrating a method of repositioning a tether to secure a prosthetic heart valve. At 860 a distal end portion of a snare device (e.g., 440, 540, 640, 740) is inserted through an incision at a first location in a ventricular wall of a heart of a patient and a distal end of the snare device is positioned within the left ventricle of the heart. At 862, a tether extending from a prosthetic mitral valve and within the left ventricle and through an incision at a second location on the ventricular wall of the heart is snared with the snare device. At 864, the tether is pulled proximally with the snare device such that a proximal end of the tether is moved back through the incision at the second location on the ventricular wall and into the left ventricle. At 866, the snare device is pulled proximally such that the proximal end of the tether is pulled proximally through the incision at the first location in the ventricular wall of the heart. At 868, a tension on the tether can be adjusted. At 870, the tether can be secured at the first location on the ventricular wall of the heart with an epicardial pad device.

Figure 22:
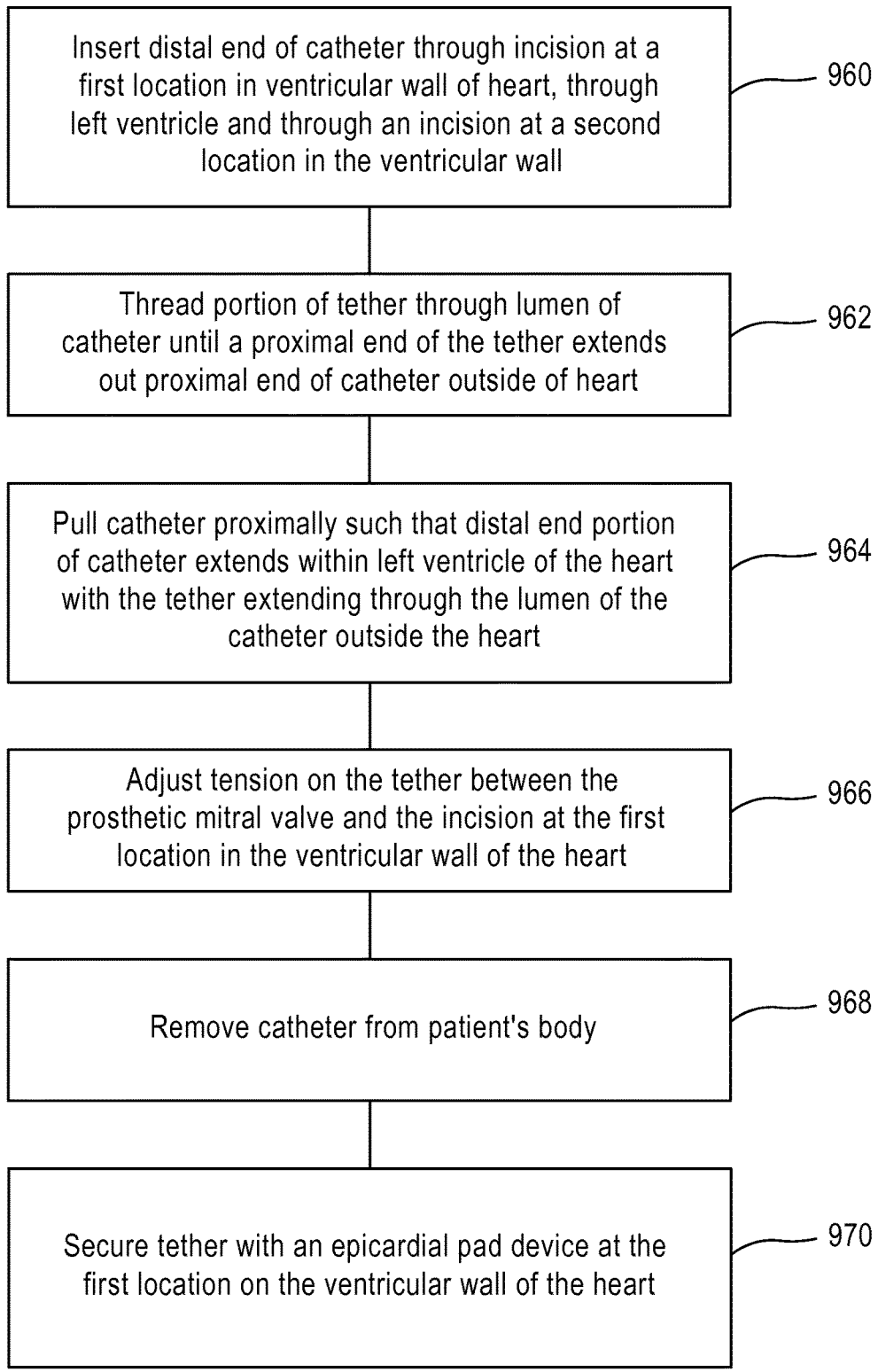

FIG. 22 is a flowchart illustrating another method of repositioning a tether to secure a prosthetic heart valve. At 960, a distal end portion of a catheter is inserted through an incision at a first location in a ventricular wall of a heart, through a left ventricle of the heart and through an incision at a second location in the ventricular wall while a proximal end of the catheter remains outside the incision at the first location, and such that a distal end portion of the catheter is disposed at least partially parallel to a tether extending through the incision at the second location in the ventricular wall. The tether is coupled at a distal end to a prosthetic mitral valve implanted within the heart. At 962, at least a portion of the tether is threaded through a lumen defined by the catheter until a proximal end of the tether extends out of a proximal end of the catheter outside of the heart. At 964, the catheter is pulled proximally such that the distal end portion of the catheter extends within the left ventricle of the heart with the tether extending through the lumen of the catheter outside of the heart. At 966, a tension on the tether between the prosthetic mitral valve and the incision at the first location in the ventricular wall of the heart can be adjusted. At 968, the catheter can be removed from the patient's body. At 970, the tether can be secured at the first location on the ventricular wall of the heart with an epicardial pad device.

Figure 23:
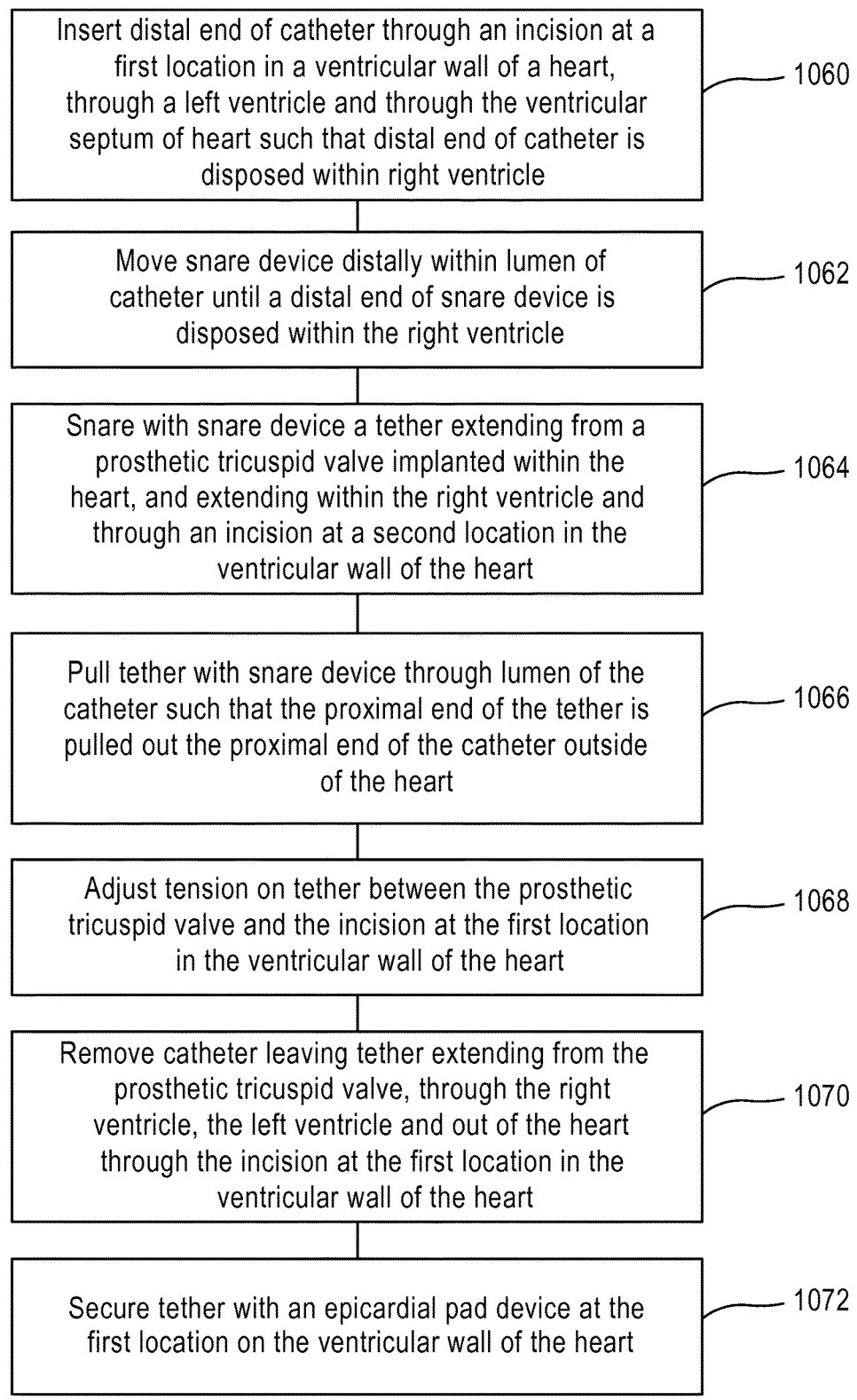

FIG. 23 is a flowchart illustrating another method of repositioning a tether to secure a prosthetic heart valve. At 1060, a distal end of a catheter is inserted through an incision at a first location in a ventricular wall of a heart, through a left ventricle of the heart and through the ventricular septum of the heart such that the distal end of the catheter is disposed within the right ventricle. A portion of the catheter extends through the incision at the first location with the proximal end of the catheter disposed outside the heart. At 1062, a snare device is moved distally within a lumen of the catheter until a distal end of the snare device is disposed within the right ventricle. At 1064, a tether extending from a prosthetic tricuspid valve implanted within the heart, and extending within the right ventricle and through an incision at a second location in the ventricular wall of the heart is snared with the snare device. At 1066, tether is pulled with the snare device through the lumen of the catheter such that the proximal end of the tether is pulled out the proximal end of the catheter outside of the heart. At 1068, a tension on the tether between the prosthetic tricuspid valve and the incision at the first location in the ventricular wall of the heart can be adjusted. At 1070, the catheter can be removed from the patient's body leaving the tether extending from the prosthetic tricuspid valve, through the right ventricle, the left ventricle and out of the heart through the incision at the first location in a ventricular wall of a heart. At 1072, the tether can be secured at the first location on the ventricular wall of the heart with an epicardial pad device.

Figure 24:
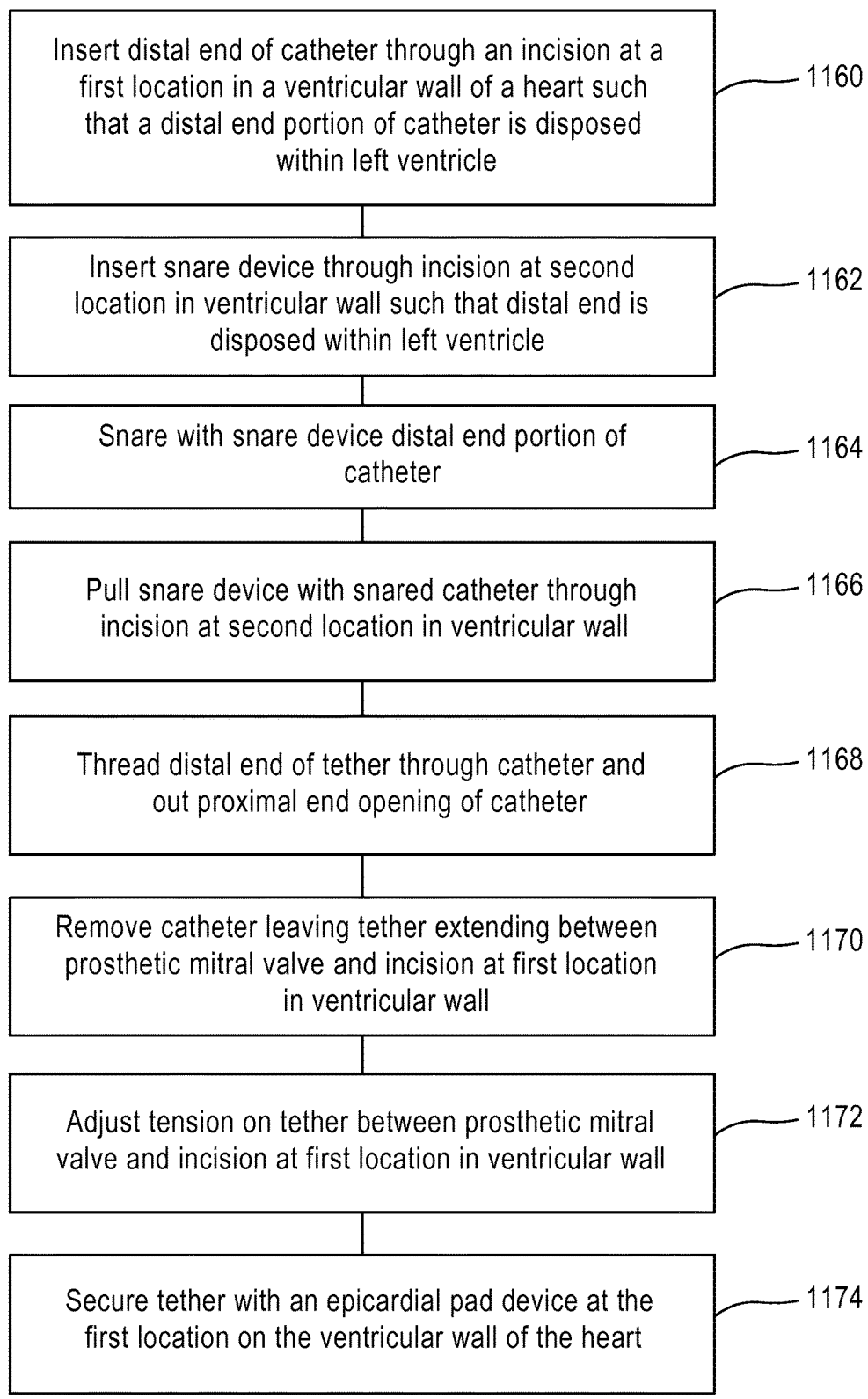
FIG. 24 is a flowchart illustrating another method of repositioning a tether to secure a prosthetic heart valve.

FIG. 24 is a flowchart illustrating another method of repositioning a tether to secure a prosthetic heart valve. At 1160, a distal end of a catheter is inserted through an incision at a first location in a ventricular wall of a heart and disposed within a left ventricle of the heart. At 1162, a snare device is inserted through an incision at a second location in the ventricular wall of the heart such that a distal end portion of the snare device is disposed with the left ventricle of the heart. A tether extends from a prosthetic mitral valve, through the left ventricle out through the incision at the second location in the ventricular wall of the heart. At 1164, the distal end portion of the catheter is snared with the snare device. At 1166, the snare device is pulled along with the snared distal end portion of the catheter through the incision at the second location in the ventricular wall, while a proximal end of the catheter remains outside the incision at the first location. At 1168, a distal end of the tether is threaded through a distal opening defined by the catheter, through a lumen defined by the catheter and out a proximal opening defined by the catheter. At 1170, the catheter is removed, leaving the tether extending through the incision at the first location in the ventricular wall of the heart. At 1172, a tension on the tether between the prosthetic mitral valve and the incision at the first location in the ventricular wall of the heart can be adjusted. At 1174, the tether can be secured at the first location on the ventricular wall of the heart with an epicardial pad device.

In other embodiments, there may be additional positioning-tethers optionally attached to the prosthetic valve to provide additional control over position, adjustment, and compliance during deployment and possible for up to 30 days afterwards to ensure there is no leaking. It is contemplated that the positioning tethers may be kept and gathered outside of the patient body for a period of time until the interventionalist can verify by Echocardiography or Fluoroscopy that no further adjustment is necessary.

During deployment, the operator is able to adjust or customize the tethers to the correct length for a particular patient's anatomy. The tethers also allow the operator to tighten the cuff onto the tissue around the valvular annulus by pulling the tethers, which creates a leak-free seal.

In some embodiments, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers described herein can be made from surgical-grade materials such as biocompatible polymer suture material. Examples of such material include 2-0 exPFTE (polytetrafluoroethylene) or 2-0 polypropylene. In one embodiment, the tethers are inelastic. It is also contemplated that one or more of the tethers may optionally be elastic to provide an even further degree of compliance of the valve during the cardiac cycle. Upon being drawn to and through the apex of the heart, the tether(s) may be fastened by a suitable mechanism such as tying off to a pledget or similar adjustable button-type epicardial anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Further, it is contemplated that the prosthetic heart valve may optionally be deployed with a combination of installation tethers and a permanent tether, attached to either the stent or cuff, or both, with the installation tethers being removed after the valve is successfully deployed. It is also contemplated that combinations of inelastic and elastic tethers may optionally be used for deployment and to provide structural and positional compliance of the valve during the cardiac cycle.

In some embodiments, to control the potential tearing of tissue at the apical entry point of the delivery system, a circular, semi-circular, or multi-part pledget is employed. The pledget may be constructed from a semi-rigid material such as PFTE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex. As described, the epicardial anchor device can include at least 1-4 subcomponents. In some embodiments, the epicardial anchor device is a rigid anchoring element. In embodiments having two components, the epicardial anchor device is contemplated as having a rigid element for securing the tether and a flexible (felt pad or pledget) element sandwiched between the rigid element and the epicardial surface to address leaking problems. In another embodiment having two components, the epicardial anchor device is contemplated as having a rigid element for securing the tether and a flexible collapsible sleeve sandwiched between the rigid element and the epicardial surface to address leaking problems. In an embodiment having three components, the epicardial anchor device is contemplated as having a rigid element for securing the tether, a flexible (felt pad or pledget) element and a flexible collapsible sleeve sandwiched between the rigid element and the epicardial surface to address leaking problems. As a fourth component, any of these embodiments may include a tension meter or tether strain gauge as described above, for example, with respect to FIGS. 5 and 6. As a fifth component, any of these embodiments, may include a system for adjusting the length of the tether.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A method, comprising:
   inserting a distal end portion of a snare device through an incision at a first location in a ventricular wall of a heart of a patient and positioning a distal end of the snare device in a left ventricle of the heart;
   snaring with the snare device a tether at least partially disposed within the left ventricle, the tether exiting the heart at an incision at a second location on the ventricular wall of the heart and extending from a prosthetic mitral valve implanted within a mitral annulus of the heart;
   pulling the tether with the snare device such that a proximal end of the tether is moved back through the incision at the second location on the ventricular wall and into the left ventricle; and
   pulling the snare device proximally, such that the snared tether is pulled proximally through the incision at the first location in the ventricular wall of the heart.

2. The method of claim 1, further comprising:
   after the pulling the snare device, securing the tether at the first location on the ventricular wall of the heart with an epicardial pad device.

3. The method of claim 1, further comprising:
   after the pulling the snare device, adjusting a tension on the tether extending through the incision at the first location on the ventricular wall of the heart.

4. The method of claim 3, wherein the adjusting a tension on the tether extending through the incision at the first location on the ventricular wall of the heart includes using a tensioning element coupled to the tether.

5. The method of claim 1, further comprising:
after the pulling the snare device, adjusting a tension on the tether extending through the incision at the first location on the ventricular wall of the heart; and
securing the tether at the first location on the ventricular wall of the heart.

6. The method of claim 1, further comprising:
prior to inserting the distal end portion of the snare device, inserting a catheter through the incision at the first location in the ventricular wall of the heart of the patient;
positioning a distal end portion of the catheter proximate to the second location on the ventricular wall of the heart; and
the inserting the distal end portion of the snare device through the incision at the first location in the ventricular wall of the heart of the patient includes inserting the snare device through a lumen of the catheter until the distal end of the snare device exits a distal end of the catheter proximate to the second location on the ventricular wall of the heart.

7. The method of claim 6, wherein the pulling the snare device proximally, such that the snared tether is pulled proximally through the incision at the first location in the ventricular wall of the heart, includes pulling the snare device proximally within the lumen of the catheter.

8. The method of claim 6, further comprising:
after the pulling the snare device, removing the catheter from the heart leaving the tether extending through the incision at the first location in the ventricular wall of the heart.

9. The method of claim 8, further comprising:
after removing the catheter, adjusting a tension on the tether extending through the incision at the first location on the ventricular wall of the heart.

10. The method of claim 9, further comprising:
after adjusting the tension on the tether, securing the tether at the first location on the ventricular wall of the heart.

11. The method of claim 1, further comprising:
prior to inserting the distal end portion of the snare device through the incision at the first location, inserting a delivery device through the incision at the second location in the ventricular wall, the delivery device including the prosthetic mitral valve coupled thereto; and
deploying the prosthetic mitral valve in the mitral annulus of the heart such that the tether extends from the prosthetic mitral valve and out through the incision at the second location in the ventricular wall of the heart.

12. The method of claim 1, wherein the incision at the first location is at a spaced distance from an apex region of the heart and the incision at the second location is at the apex region of the heart.

13. The method of claim 1, wherein the incision at the first location is at an apex region of the heart and the incision at the second location is at a spaced distance from the apex region of the heart.

14. The method of claim 13, further comprising:
securing the tether at the first location on the ventricular wall of the heart such that an angle between a commissural-commissural plane of the mitral annulus of the heart and the tether is substantially 90 degrees.

* * * * *